United States Patent
Kleymann et al.

(10) Patent No.: US 10,590,094 B2
(45) Date of Patent: Mar. 17, 2020

(54) AMINOTHIAZOLE DERIVATIVES USEFUL AS ANTIVIRAL AGENTS

(71) Applicant: Innovative Molecules GmbH, Bad Salzuflen (DE)

(72) Inventors: Gerald Kleymann, Bad Salzuflen (DE); Christian Gege, Ehingen (DE)

(73) Assignee: Innovative Molecules GmbH, Bad Salzuflen (DE)

(*) Notice: Subject to any disclaimer, the term of this patent is extended or adjusted under 35 U.S.C. 154(b) by 0 days.

(21) Appl. No.: 16/088,852

(22) PCT Filed: Apr. 5, 2017

(86) PCT No.: PCT/EP2017/058077
§ 371 (c)(1),
(2) Date: Sep. 27, 2018

(87) PCT Pub. No.: WO2017/174640
PCT Pub. Date: Oct. 12, 2017

(65) Prior Publication Data
US 2019/0112285 A1   Apr. 18, 2019

(30) Foreign Application Priority Data
Apr. 6, 2016 (EP) .................................. 16000787

(51) Int. Cl.
| C07D 277/54 | (2006.01) |
| C07F 9/6539 | (2006.01) |
| C07F 9/6558 | (2006.01) |
| C07F 9/40 | (2006.01) |
| C07F 9/44 | (2006.01) |

(52) U.S. Cl.
CPC .............. *C07D 277/54* (2013.01); *C07F 9/40* (2013.01); *C07F 9/44* (2013.01); *C07F 9/6539* (2013.01); *C07F 9/65583* (2013.01)

(58) Field of Classification Search
CPC .................................................. C07D 277/54
USPC ....................................................... 546/270.7
See application file for complete search history.

(56) References Cited

U.S. PATENT DOCUMENTS

| 6,150,385 | A | 11/2000 | Thaisrivongs et al. |
| 6,458,959 | B1 | 10/2002 | Crute et al. |
| 6,500,817 | B1 | 12/2002 | Fischer et al. |
| 7,105,553 | B2 | 9/2006 | Fischer et al. |
| 7,883,713 | B2 | 2/2011 | Betz et al. |
| 8,759,335 | B2 | 6/2014 | Hadida Ruah et al. |
| 8,784,887 | B2 | 7/2014 | Laich et al. |
| 2002/0119995 | A1 | 8/2002 | Hendrix et al. |
| 2002/0160932 | A1 | 10/2002 | Kleymann et al. |
| 2004/0235916 | A1 | 11/2004 | Schohe-Loop et al. |
| 2007/0004735 | A1 | 1/2007 | Betz et al. |

FOREIGN PATENT DOCUMENTS

| DE | 19959958 A1 | 8/2001 |
| DE | 10039265 A1 | 2/2002 |
| DE | 10044328 A1 | 3/2002 |
| DE | 10044358 A1 | 3/2002 |
| DE | 10129716 A1 | 1/2003 |
| DE | 10129717 A1 | 1/2003 |
| DE | 10210319 A1 | 9/2003 |
| WO | 99/42455 | 8/1999 |
| WO | 00/76966 A2 | 12/2000 |
| WO | 01/96874 A1 | 12/2001 |
| WO | 03/007946 A1 | 2/2004 |
| WO | 2004/015416 A2 | 2/2004 |

OTHER PUBLICATIONS

Espacenet bibliographic data for DE10039265 published Feb. 21, 2002, two pages.
Espacenet bibliographic data for DE10044328 published Mar. 21, 2002, two pages.
Espacenet bibliographic data for DE10044358 published Mar. 21, 2002, two pages.
Espacenet bibliograhic data for DE10129716 published Jan. 2, 2003, two pages.
Espacenet bibliographic data for DE10129717 published Jan. 2, 2003, two pages.
Espacenet bibliographic data for DE10210319 published Sep. 18, 2003, two pages.
Espacenet bibliographic data for DE19959958 published Aug. 30, 2001, two pages.
Espacenet bibliographic data for WO 00/76966 published Dec. 21, 2000, two pages.
Espacenet bibliographic data for WO 2004015416 published Feb. 19, 2004, one page.
Espacenet bibliographic data for WO 03007946 published Jan. 30, 2003, two pages.
International Search Report for corresponding PCT/EP2017/058077 dated Jul. 24, 2017, four pages.

*Primary Examiner* — Taofiq A Solola
(74) *Attorney, Agent, or Firm* — Rankin, Hill & Clark LLP

(57) ABSTRACT

The invention relates to novel compounds of the Formula (I), to a process for their preparation and to their use as medicaments, in particular as antiviral medicaments.

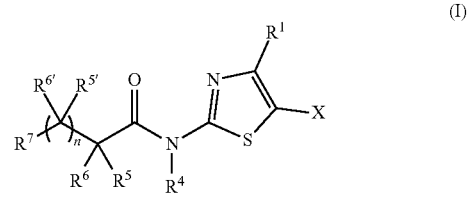

20 Claims, No Drawings

AMINOTHIAZOLE DERIVATIVES USEFUL AS ANTIVIRAL AGENTS

SUMMARY OF THE INVENTION

The present invention relates to novel compounds, to a process for their preparation and to their use as medicaments, in particular as antiviral medicaments.

INTRODUCTION

The pandemic of viral infections has plagued humanity since ancient times, causing mucocutaneous infection such as herpes labial's and herpes genitalis. Disease symptoms often interfere with everyday activities and occasionally HSV infections are the cause of life-threatening (encephalitis) or sight-impairing disease (keratitis), especially in neonates, elderly and the immunocompromised patient population such as transplant or cancer patients or patients with an inherited immunodeficiency syndrome or disease. After infection the alpha herpesviridae persist for life in neurons of the host in a latent form, periodically reactivating and often resulting in significant psychosocial distress for the patient. Currently no cure is available.

So far, vaccines, interleukins, interferones, therapeutic proteins, antibodies, immunomodulators and small-molecule drugs with specific or non-specific modes of action lacked either efficacy or the required safety profile to replace the nucleosidic drugs acyclovir, valacyclovir and famciclovir as the first choice of treatment.

The known thiazolylamides are the most potent drugs in development today. These antiviral agents act by a novel mechanism of action and display low resistance rates in vitro and superior efficacy in animal models compared to nucleosidic drugs, however, development is hampered by off target carbonic anhydrase activity and an unusual pharmacokinetic profile.

This patent application discloses new antiviral compounds lacking (or at least with significantly reduced) carbonic anhydrase activity, showing an improved solubility and a suitable pharmacokinetic profile for use as a medicament.

PRIOR ART

2-Aminothiazol-5-sulfonamides are known from the publication C. Ziegler et al., J. Org. Chem. 25, 1960, 1454-1455. Moreover, the German Offenlegungsschrift 2101640 describes N-Thiazol-2-yl-amides and ureas having herbicidal action.

WO97/24343 relates to phenylthiazole derivates having anti-Herpesvirus properties.

WO99/42455 likewise relates to phenylthiazole derivates having anti-Herpesvirus properties.

WO99/47507 relates to 1,3,4-Thiadiazoles derivates having anti-Herpesvirus properties.

WO0147904 (A1) and the corresponding US2004/0006076 relate to thiazolyl amides having anti-Herpesvirus properties.

WO2003/000259 relates to topical application of thiazolyl amides.

WO2004060860 (A2) relates to a method for inhibiting the replication of Herpesviruses.

WO0220014 (A1) relates to uncompetitive inhibitors of helicase-primase.

WO0212211 (A1) relates to inverse thiazolylamide derivatives.

WO0053591 (A1) relates to thiazolyl urea derivatives and their utilization as antiviral agents.

WO03000260 (A1) relates to thiazolyl amides and their use as antiviral drugs.

WO0196874 (A1) and EP1319185 (A1) relate to a method for identifying compounds with anti-Herpes activity.

WO2004015416 relates to methods for the identification of agents with anti-microbial action.

WO03007946 relates to secondary 1,3-thiazole-5-yl sulfonamide derivatives and their use as antiviral agents.

WO0076966 relates to indolinylamide derivatives.

DE19959958 relates to new 2-ureido-thiazole-5-sulfonic acid amide derivatives useful as antiviral agents, especially against herpes simplex infections.

DE10210319 relates to new thiazole-5-sulfonamide derivatives, useful for the treatment of viral infections in humans and animals, especially herpes simplex or human cytomegalovirus infections.

DE10129717 relates to a combination preparation containing nucleoside compound and 5-sulfonyl-2-phenylacetamido-thiazole derivative, useful as antiviral agent effective against herpes viruses, especially herpes simplex.

DE10129716 relates to a combination preparation useful as antiviral agent effective against herpes viruses, especially herpes simplex, contains acetylsalicylic acid and 5-sulfonyl-2-phenylacetamido-thiazole derivative.

DE10044358 relates to new thiazole-5-sulfonamide derivatives useful as antiviral agents, especially for control of herpes simplex infections.

DE10044328 relates to new thiazole-5-sulfonamide derivatives useful as antiviral agents, especially for control of herpes simplex infections.

DE10039265 relates to new 2-acylamino-5-aminosulfonyl-1,3-thiazole derivatives, useful as antiviral agents, especially for treatment or prophylaxis of herpes simplex virus infections.

HRP20140352 relate to N-[5-aminosulfonyl)-4-methyl-1,3-thiazol-2-yl]-N-methyl-2-[4-(2-pyridinyl)phenyl]acetamide mesylate monohydrate.

WO2006103011 and EP1865921 relate to a pharmaceutical preparation of N-[5-(Aminosulfonyl)-4-methyl-1,3-thiazol-2-yl]-N-methyl-2-[4-(2-pyridinyl)phenyl]acetamide.

WO2005075435 relates to compounds being ATP-binding cassette transporter modulators useful in the treatment of i.a. cystic fibrosis and Alzheimer's disease.

In summary, none of the cited prior art covers aminosulfonimidoyl, methyl-sulfonimidoyl, methylsulfinyl, methylsulfanyl, methyl-5-sulfinamoyl, cyanosulfamoyl, N-cyano-S-methyl-sulfonimidoyl, 5-diaminophosphoryl, phosphonamidic acid or phosphonic acid, derivatives of the thiazolylacetamide series. Thus, the invention is new and the novel compounds show no or at least significantly reduced off target carbonic anhydrase activity at increased solubility. The optimised pharmacokinetic profile of selected compounds leads to a profound antiviral activity in treated mammals suitable for clinical development in humans and use as a medicament.

DETAILED DESCRIPTION OF THE INVENTION

The present invention relates to thiazolyl amide derivatives of the general Formula (I)

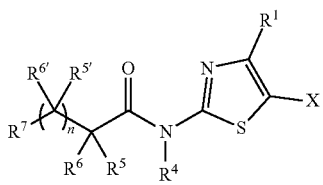

(I)

an enantiomer, diastereomer, tautomer, N-oxide, solvate, formulation and pharmaceutically acceptable salt thereof, wherein
X is selected from

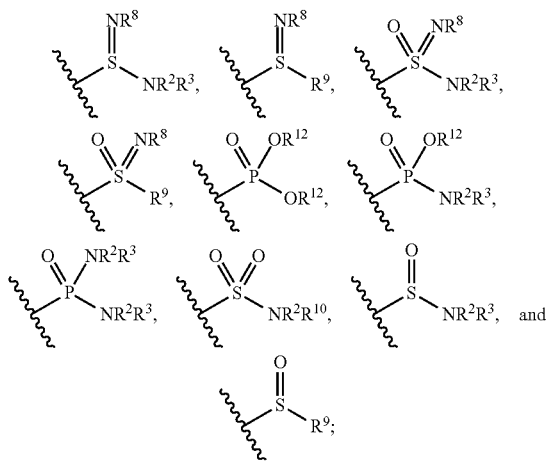

$R^1$ is selected from H, halogen, $C_{1-6}$-alkyl, halo-$C_{1-6}$-alkyl, $C_{3-6}$-cycloalkyl, halo-$C_{3-6}$-cycloalkyl,
preferably with the proviso that in the case that X is one of

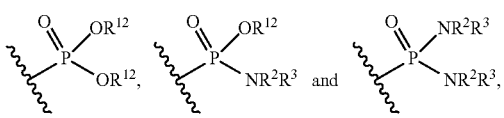

then $R^1$ is not hydrogen (H)

$R^2$ is selected from H, —CN, —NO$_2$, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6- to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-$C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)N$^{11}$R$^{12}$, ($C_{0-10}$-alkylene-NR$^{11}$C(=S)) R$^{11}$R$^{12}$, $C_{0-10}$-alkylene-N$^{11}$SO$_2$NR$^{11}$, $C_{0-10}$-alkylene-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O) NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C (=O)R$^{11}$, NR$^{11}$SO$_2$R$^{13}$, NR$^{11}$C(=O)NR$^{11}$R$^{12}$, NR$^{11}$SO$_2$NR$^{11}$R$^{12}$, $C_{3-10}$-cycloalkyl, O—$C_{3-10}$-cycloalkyl, $C_{3-10}$-heterocycloalkyl, O—$C_{3-10}$-heterocycloalkyl and NR$^{11}$R$^{12}$;

$R^3$ is selected from H, $C_{1-6}$-alkyl, halo-$C_{1-6}$-alkyl, —O-halo-$C_{1-6}$-alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from halogen, —CN, OH, oxo, $C_{1-3}$-alkyl, O-halo-$C_{1-3}$-alkyl, SO$_2$—$C_{1-3}$-alkyl, CO$_2$H;

or $R^2$ and $R^3$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, O-halo-$C_{1-3}$-alkyl, SO$_2$—$C_{1-3}$-alkyl, CO$_2$H;

$R^4$ is selected from H, $C_{1-6}$-alkyl, $C_{1-6}$-acyl, $C_{2-6}$-alkenyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, $C_{1-3}$-alkyl, O—$C_{1-3}$-alkyl, O-halo-$C_{1-3}$-alkyl;

$R^5$ and $R^6$ and $R^{5'}$ and $R^{6'}$ are independently selected from H, halogen, $C_{1-6}$-alkyl, NH$_2$, NHC$_{1-6}$-alkyl, N(C$_{1-6}$-alkyl)$_2$, $C_{0-6}$-alkylene-C(=O)NH$_2$;

or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, halo-$C_{1-3}$-alkyl, O-halo-$C_{1-3}$-alkyl, SO$_2$—$O_{1-3}$-alkyl, CO$_2$H;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —ON, —NO$_2$, OH, oxo, $C_{1-3}$-alkyl, halo-$C_{1-3}$-alkyl, 0-$C_{1-3}$-alkyl, SO$_2$—$C_{1-3}$-alkyl, CO$_2$H;

$R^7$ is selected from a 6-membered aryl and 5- or 6-membered heteroaryl, wherein aryl and heteroaryl are optionally substituted with 1 to 4 substituents independently selected from halogen, —ON, —NO$_2$, OH, $C_{1-6}$-alkyl, O—$C_{1-6}$-alkyl, $C_{3-6}$-cycloalkyl, O—$C_{3-6}$-cycloalkyl, $C_{3-6}$-heterocycloalkyl, O—$C_{3-6}$-heterocycloalkyl, SO$_y$—$C_{1-6}$-alkyl, CO$_2$H, C(=O)O—$O_{1-6}$-alkyl, 6- to 10-membered aryl, 5- or 10-membered heteroaryl, O-(6- to 10-membered aryl) and O-(5- or 10-membered heteroaryl), wherein alkyl, cycloalkyl, heterocycloalkyl, aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O)NR$^{11}$R$^{12}$, NR$^{11}$C(=O)OR$^{13}$, OC(=O)NR$^{11}$R$^{12}$, C(=S)NR$^{11}$R$^{12}$, NR$^{11}$C(=S)NR$^{11}$R$^{12}$, NR$^{11}$C(=S)OR$^{13}$OC(=S) NR$^{11}$R$^{12}$; SO$_y$—$O_{1-6}$-alkyl, SO$_y$-halo-$C_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$;

$R^8$ is selected from H, —CN, —NO$_2$, C$_{1-10}$-alkyl, C$_{2-10}$-alkenyl, C$_{2-10}$-alkynyl, C$_{0-10}$-alkylene-C$_{3-10}$-cycloalkyl, C$_{0-10}$-alkylene-C$_{3-10}$-heterocycloalkyl, C$_{0-10}$-alkylene-(5 to 10-membered heteroaryl), C$_{0-10}$-alkylene-(6 to 10-membered aryl), C$_{0-10}$-alkylene-(6 to 10-membered heteroaryl), C$_{0-10}$-alkylene-OR$^{11}$, C$_{0-10}$-alkylene-CO$_2$R$^{11}$, C$_{0-10}$-alkylene-C(=O)NR$^{11}$R$^{12}$, C$_{0-10}$-alkylene-C(=S)NR$^{11}$R$^{12}$, C$_{0-10}$-alkylene-C(=O)NR$^{11}$SO$_2$R$^{13}$, C$_{0-10}$-alkylene-C(=S)NR$^{11}$SO$_2$R$^{11}$, C$_{0-10}$-alkylene-C(=O)R$^{11}$, C$_{0-10}$-alkylene-C(=S)R$^{11}$, C$_{0-10}$-alkylene-SR$^{11}$, C$_{0-10}$-alkylene-SO$_x$R$^{13}$, C$_{0-10}$-alkylene-SO$_3$R$^{11}$, C$_{0-10}$-alkylene-SO$_2$NR$^{11}$R$^{12}$, C$_{0-10}$-alkylene-NR$^{11}$C(=O)R$^{11}$, C$_{0-10}$-alkylene-NR$^{11}$C(=S)R$^{11}$, C$_{0-10}$-alkylene-NR$^{11}$SO$_2$R$^{11}$, C$_{0-10}$-alkylene-NR$^{11}$C(=O)NR$^{11}$R$^{12}$, C$_{0-10}$-alkylene-NR$^{11}$C(=S)NR$^{11}$R$^{12}$, C$_{0-10}$-alkylene-NR$^{11}$—SO$_2$—NR$^{11}$R$^{12}$, C$_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—C$_{2-6}$-alkylene-OR$^{11}$, C$_{1-6}$-alkyl, halo-C$_{1-6}$-alkyl, halogen, CO$_2$R$^{11}$, CONR$^{11}$R$^{12}$, CONR$^{11}$SO$_2$R$^{11}$, COR$^{11}$, SO$_x$R$^{11}$, SO$_3$H, PO(OH)$_2$, SO$_2$NR$^{11}$R$^{12}$, NR$^{11}$COR$^{11}$, NR$^{11}$SO$_2$R$^{11}$, NR$^{11}$—CO—NR$^{11}$R$^{12}$, NR$^{11}$—SO$_2$—NR$^{11}$R$^{12}$, C$_{3-10}$-cycloalkyl, O—C$_{3-10}$-cycloalkyl, C$_{3-10}$-heterocycloalkyl, O—C$_{3-10}$-heterocycloalkyl and NR$^{11}$R$^{12}$;

$R^9$ is selected from C$_{1-10}$-alkyl, C$_{2-10}$-alkenyl, C$_{2-10}$-alkynyl, C$_{0-10}$-alkylene-C$_{3-10}$-cycloalkyl, C$_{0-10}$-alkylene-C$_{3-10}$-heterocycloalkyl, C$_{0-10}$-alkylene-(5- to 10-membered heteroaryl), C$_{0-10}$-alkylene-(6- to 10-membered aryl), C$_{0-10}$-alkylene-(6- to 10-membered heteroaryl), C$_{0-10}$-alkylene-OR$^{11}$, C$_{0-10}$-alkylene-CO$_2$R$^{11}$, C$_{0-10}$-alkylene-C(=O)NR$^{11}$R$^{12}$, C$_{0-10}$-alkylene-C(=S)NR$^{11}$R$^{12}$, C$_{0-10}$-alkylene-C(=O)NR$^{11}$SO$_2$R$^{13}$, C$_{0-10}$-alkylene-C(=S)NR$^{11}$SO$_2$R$^{11}$, C$_{0-10}$-alkylene-C(=O)R$^{11}$, C$_{0-10}$-alkylene-C(=S)R$^{11}$, C$_{0-10}$-alkylene-SR$^{11}$, C$_{0-10}$-alkylene-SO$_x$R$^{13}$, C$_{0-10}$-alkylene-SO$_3$R$^{11}$, C$_{0-10}$-alkylene-SO$_2$NR$^{11}$R$^{12}$, C$_{0-10}$-alkylene-NR$^{11}$C(=O)R$^{11}$, C$_{0-10}$-alkylene-NR$^{11}$C(=S)R$^{11}$, C$_{0-10}$-alkylene-NR$^{11}$SO$_2$R$^{13}$, C$_{0-10}$-alkylene-NR$^{11}$C(=O)NR$^{11}$R$^{12}$, C$_{0-10}$-alkylene-NR$^{11}$C(=S)NR$^{11}$R$^{12}$, C$_{0-10}$-alkylene-NR$^{11}$SO$_2$NR$^{11}$R$^{12}$, C$_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, —NO$_2$, OR$^{11}$, O—C$_{2-6}$-alkylene-OR$^{11}$, C$_{1-6}$-alkyl, halo-C$_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$, NR$^{11}$C(=O)NR$^{11}$R$^{12}$, NR$^{11}$SO$_2$NR$^{11}$R$^{12}$, C$_{3-10}$-cycloalkyl, O—C$_{3-10}$-cycloalkyl, C$_{3-10}$-heterocycloalkyl, O—C$_{3-10}$-heterocycloalkyl and NR$^{11}$R$^{12}$;

$R^{10}$ is selected from —CN, OH, and —NO$_2$;

$R^{11}$ is independently selected from H, C$_{0-6}$-alkylene-C$_{3-10}$-cycloalkyl and C$_{0-6}$-alkylene-C$_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, C$_{1-3}$-alkyl, halo-C$_{1-3}$-alkyl, O—C$_{1-3}$-alkyl, O-halo-C$_{1-3}$-alkyl, NH$_2$, NH(C$_{1-3}$-alkyl), N(C$_{1-3}$-alkyl)$_2$, C$_{3-6}$-heterocycloalkyl, C$_{3-6}$-cycloalkyl, SO$_2$—NHC$_{1-3}$-alkyl, SO$_2$—N(O$_{1-3}$-alkyl)$_2$ and SO$_2$—C$_{1-3}$-alkyl, wherein cycloalkyl and heterocycloalkyl is unsubstituted or substituted with 1 to 3 substituents independently selected from the group consisting of F, OH, oxo, CH$_3$, CHF$_2$ and CF$_3$;

$R^{12}$ is independently selected from H, C$_{1-6}$-alkyl, halo-C$_{1-6}$-alkyl and C$_{3-6}$-cycloalkyl;

or $R^{11}$ and $R^{12}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, C$_{1-3}$-alkyl, O—C$_{1-3}$-alkyl, O-halo-C$_{1-3}$-alkyl, SO$_2$—C$_{1-3}$-alkyl, CO$_2$H;

$R^{13}$ is independently selected from C$_{1-6}$-alkyl, C$_{0-6}$-alkylene-C$_{3-10}$-cycloalkyl and C$_{0-6}$-alkylene-C$_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, C$_{1-3}$-alkyl, halo-C$_{1-3}$-alkyl, O—C$_{1-3}$-alkyl, O-halo-C$_{1-3}$-alkyl, NH$_2$, NH(C$_{1-3}$-alkyl), N(C$_{1-3}$-alkyl)$_2$, C$_{3-6}$-heterocycloalkyl, C$_{3-6}$-cycloalkyl, SO$_2$—NHC$_{1-3}$-alkyl, SO$_2$—N(C$_{1-3}$-alkyl)$_2$ and SO$_2$—C$_{1-3}$-alkyl, wherein cycloalkyl and heterocycloalkyl is unsubstituted or substituted with 1 to 3 substituents independently selected from the group consisting of F, OH, oxo, CH$_3$, CHF$_2$ and CF$_3$;

n is selected from 0 and 1;

x is independently selected from 1 and 2;

y is independently selected from 0, 1 and 2;

and wherein optionally $R^1$ is connected to one residue selected from $R^2$, $R^3$, $R^8$, $R^9$, $R^{10}$ or $R^{12}$ to form a 5 to 8-membered heterocycle, which is optionally substituted with 1 to 4 substituents independently selected from the group consisting of halogen, —CN, —NO$_2$, OH, oxo, C$_{1-3}$-alkyl, halo-C$_{1-3}$-alkyl, O—C$_{1-3}$-alkyl, O-halo-C$_{1-3}$-alkyl, SO$_2$—C$_{1-3}$-alkyl, CO$_2$H.

In the context of the present invention "C$_{1-10}$-alkyl" means a saturated alkyl chain having 1 to 10 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl and decyl. Preferred is "C$_{1-6}$-alkyl", more preferred is "C$_{1-4}$-alkyl", most preferred is "C$_{1-3}$-alkyl".

The term "halo-C$_{1-10}$-alkyl" or "halo-C$_{1-6}$-alkyl", respectively, means that one or more hydrogen atoms in the alkyl chain are replaced by a halogen, as defined below. A preferred example thereof is the formation of a —CF$_3$ group.

"C$_{2-10}$-alkenyl" means an alkyl chain having 1 to 10 carbon atoms which may be straight chained or branched, containing at least one carbon to carbon double bond. Examples thereof include ethenyl, propenyl, decenyl, 2-methylenehexyl and (2E,4E)-hexa-2,4-dienyl. Preferred is "C$_{2-6}$-alkenyl".

"C$_{2-10}$-alkynyl" means an alkyl chain having 1 to 10 carbon atoms which may be straight chained or branched, containing at least one carbon to carbon triple bond. Examples thereof include ethynyl, propynyl and decynyl. Preferred is "C$_{2-6}$-alkynyl".

A "C$_{0-10}$-alkylene" means that the respective group is divalent and connects the attached residue with the remaining part of the molecule. Moreover, in the context of the present invention, "C$_0$-alkylene" is meant to be represent a bond. Preferred is "C$_{0-6}$-alkylene".

A C$_{3-10}$-cycloalkyl group or C$_{3-10}$-carbocycle means a saturated or partially unsaturated mono-, bi-, spiro- or multicyclic ring system comprising 3 to 10 carbon atoms.

Examples include cyclopropyl, cyclobutyl, cyclopentyl, cyclohexyl, cyclohexenyl, bicyclo[2.2.2]octyl, bicyclo[2.2.1]heptyl, adamantyl and pentacyclo[4.2.0.0$^{2,5}$.0$^{3,8}$.0$^{4,7}$]octyl. Preferred is a $C_{3-6}$-cycloalkyl group. More preferred is a cyclopropyl-group.

A $C_{3-10}$-heterocycloalkyl group means a saturated or partially unsaturated 3 to 10 membered carbon mono-, bi-, spiro- or multicyclic ring wherein 1, 2 or 3 carbon atoms are replaced by 1, 2 or 3 heteroatoms, respectively, wherein the heteroatoms are independently selected from N, O, S, SO and $SO_2$. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected via a carbon or nitrogen atom. Preferred is a $C_{3-6}$-heterocycloalkyl group.

A 5- to 10-membered mono- or bicyclic heteroaromatic ring system (within the application also referred to as heteroaryl) containing up to 5 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. Preferred are 5- to 6-membered monocyclic heteroaromatic rings. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl and pyrazolo[1,5-a]pyrimidinyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

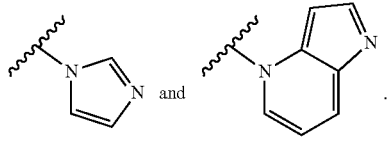 [SMILES: *n1ccnc1 ; "and" ; *n1cccc2nccc1-2]

A 6- to 10-membered mono- or bicyclic aromatic ring system (within the application also referred to as aryl) means an aromatic carbon cycle such as phenyl or naphthalenyl. Preferred are 5- to 6-membered aromatic rings (aryl), such as in particular phenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine, preferred are fluorine and chlorine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

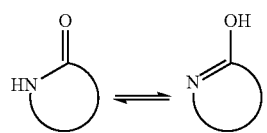

A $C_{3-10}$-cycloalkyl or $C_{3-10}$-heterocycloalkyl group can be connected straight or spirocyclic, e.g. when cyclohexane is substituted with the heterocycloalkyl group oxetane, the following structures are possible:

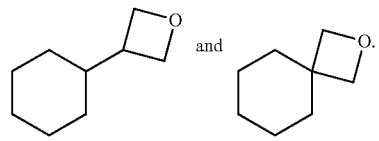 [SMILES: C1CCC(C2COC2)CC1 ; "and" ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Depending on the substitution pattern, the compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereoisomerically uniform components in a known manner.

The scope of the invention includes those compounds which are only converted into the actual active compounds of the Formulas (I) and (II) once inside the body (so-called prodrugs).

The invention relates in particular to the following embodiments:

A particularly preferred embodiment of the invention relates to compounds of Formula (I) as defined above or of Formula (II) as defined below, wherein
X is selected from the group consisting of

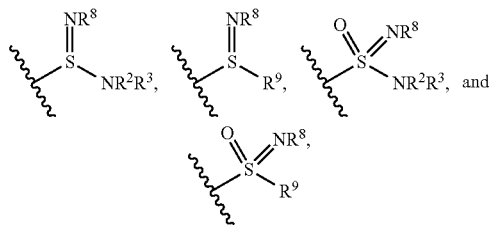

and/or from the group consisting of

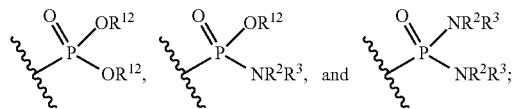

with the proviso that then R1 is not hydrogen (H); and/or from the group consisting of

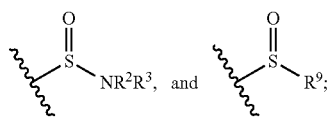

and wherein $R^1$, $R^2$, $R^3$, $R^4$, $R^5$, $R^6$, $R^{5'}$, $R^{6'}$, $R^7$, $R^8$, $R^9$, $R^{10}$, $R^{11}$, $R^{12}$, $R^{13}$, n, x and y have the meaning as defined in any of the embodiments described herein.

An even more preferred embodiment of the invention relates to compounds of Formula (I) as defined above or of Formula (II) as defined below, wherein
X is selected from the group consisting of

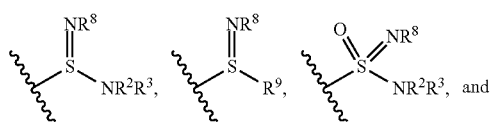

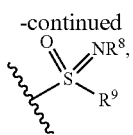

and wherein $R^1$, $R^2$, $R^3$, $R^4$, $R^5$, $R^6$, $R^{5'}$, $R^{6'}$, $R^7$, $R^8$, $R^9$, $R^{10}$, $R^{11}$, $R^{12}$, $R^{13}$, n, x and y have the meaning as defined in any of the embodiments described herein.

It is further particularly preferred embodiment relates to compounds of Formula (I) as defined above, wherein
$R^4$ is selected from $C_{1-6}$-alkyl, $C_{1-6}$-acyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl;

$R^5$ and $R^6$ and $R^{5'}$ and $R^{6'}$ are independently selected from H and $C_{1-3}$-alkyl;

or $R^5$ and $R^6$ and $R^{6'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, OH, oxo, Me (—$CH_3$), OMe (—O—$CH_3$), $CHF_2$, $CF_3$, $OCHF_2$, $OCF_3$;

or $R^6$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of halogen, OH, oxo, Me (—$CH_3$), OMe (—O—$CH_3$), $CHF_2$, $CF_3$, $OCHF_2$, $OCF_3$;

$R^7$ is selected from a 6-membered aryl and 5- or 6-membered heteroaryl, wherein aryl and heteroaryl are optionally substituted with 1 to 3 substituents independently selected from halogen, OH, Me (—$CH_3$), OMe (—O—$CH_3$), $CHF_2$, $CF_3$, $OCHF_2$, $OCF_3$ and substituted with 6-membered aryl and 5- or 6-membered heteroaryl, wherein aryl and heteroaryl are optionally substituted with 1 to 5 substituents independently selected from halogen, —ON, —$NO_2$, OH, $R^{13}$, $OR^{13}$, $CO_2R^{11}$, $NR^{11}R^{12}$, C(=O)$R^{11}$, C(=S)$R^{11}$, C(=O)$NR^{11}R^{12}$, $NR^{11}$C(=O)$NR^{11}R^{12}$, $NR^{11}$C(=O)$OR^{13}$, OC(=O)$NR^{11}R^{12}$, C(=S)$NR^{11}R^{12}$, $NR^{11}$C(=S)$NR^{11}R^{12}$, $NR^{11}$C(=S)$OR^{13}$, OC(=S)$NR^{11}R^{12}$; $SO_y$—$C_{1-6}$-alkyl, $SO_y$-halo-$C_{1-6}$-alkyl, $SR^{11}$, $SO_xR^{13}$, $SO_3R^{11}$, $SO_2NR^{11}R^{12}$, $NR^{11}SO_2R^{13}$, $NR^{11}SO_2NR^{11}R^{12}$;

and wherein the remaining substituents have the meaning as defined in any of the embodiments described herein.

In a further preferred embodiment in combination with any of the above or below embodiments $R^4$ is selected from $C_{1-6}$-alkyl, $C_{1-6}$-acyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, halo-$C_{1-3}$-alkyl, O—$C_{1-3}$-alkyl, O-halo-$C_{1-3}$-alkyl.

In a more preferred embodiment in combination with any of the above or below embodiments $R^4$ is selected from $C_{1-3}$-alkyl and halo-$C_{1-3}$-alkyl.

In an even more preferred embodiment in combination with any of the above or below embodiments $R^4$ is selected from Me (—CH$_3$).

In an alternative preferred embodiment in combination with any of the above or below embodiments $R^5$ and $R^6$ and $R^{5'}$ and R6' are independently selected from H, halogen, C$_{1-6}$-alkyl, NH$_2$, NHC$_{1-6}$-alkyl, N(C$_{1-6}$-alkyl)$_2$, C$_{0-6}$-alkylene-C(=O)NH$_2$;

or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, C$_{1-3}$-alkyl, O—C$_{1-3}$-alkyl, O-halo-C$_{1-3}$-alkyl, SO$_2$—C$_{1-3}$-alkyl, CO$_2$H;

or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, C$_{1-3}$-alkyl, O-halo-C$_{1-3}$-alkyl, SO$_2$—C$_{1-3}$-alkyl, CO$_2$H.

In a more preferred embodiment in combination with any of the above or below embodiments $R^5$ and $R^6$ and $R^{5'}$ and $R^{6'}$ are independently selected from H, C$_{1-3}$-alkyl and halo-C$_{1-3}$-alkyl.

In an even more preferred embodiment in combination with any of the above or below embodiments $R^5$ and $R^6$ and $R^{5'}$ and $R^{6'}$ are hydrogens.

In yet another alternative preferred embodiment in combination with any of the above or below embodiments $R^7$ is selected from a 6-membered aryl and 5- or 6-membered heteroaryl, wherein aryl and heteroaryl are optionally substituted with 1 to 4 substituents independently selected from halogen, —CN, —NO$_2$, OH, C$_{1-6}$-alkyl, O—C$_{1-6}$-alkyl, C$_{3-6}$-cycloalkyl, O—C$_{3-6}$-cycloalkyl, C$_{3-6}$-heterocycloalkyl, O—C$_{3-6}$-heterocycloalkyl, SO$_y$—C$_{1-6}$-alkyl, CO$_2$H, C(=O) O—C$_{1-6}$-alkyl, 6- to 10-membered aryl, 5- or 10-membered heteroaryl, O-(6- to 10-membered aryl) and O-(5- or 10-membered heteroaryl), wherein alkyl, cycloalkyl, heterocycloalkyl, aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O) NR$^{11}$R$^{12}$, NR$^{11}$C(=O)OR$^{13}$, OC(=O)NR$^{11}$R$^{12}$, C(=S) NR$^{11}$R$^{12}$, NR$^{11}$C(=S)NR$^{11}$R$^{12}$, NR$^{11}$C(=S)OR$^{13}$, OC(=S)NR$^{11}$R$^{12}$; SO$_y$—C$_{1-6}$-alkyl, SO$_y$-halo-C$_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$.

In a more preferred embodiment in combination with any of the above or below embodiments $R^7$ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O) NR$^{11}$R$^{12}$, NR$^{11}$C(=O)OR$^{13}$, OC(=O)NR$^{11}$R$^{12}$, C(=S) NR$^{11}$R$^{12}$, NR$^{11}$C(=S)NR$^{11}$R$^{12}$, NR$^{11}$C(=S)OR$^{13}$, OC(=S)NR$^{11}$R$^{12}$; SO$_y$—C$_{1-6}$-alkyl, SO$_y$-halo-C$_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$.

In an even more preferred embodiment in combination with any of the above or below embodiments $R^7$ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, OH, Me (—CH$_3$), OMe (—O—CH$_3$), CHF$_2$, CF$_3$, OCHF$_2$, OCF$_3$.

Particularly preferred are compounds of Formula (I) as defined in any of the embodiments above, wherein $R^7$ is phenyl, optionally substituted with 1 to 4 substituents (R$^x$), which independently have the meaning as defined in any of the embodiments described herein for the possible substituents of $R^7$ and which is represented by Formula (II)

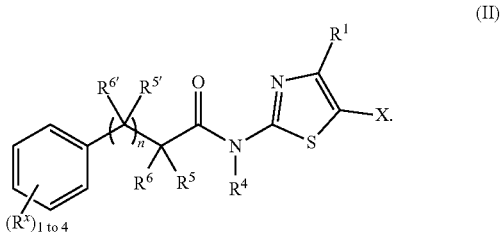

In an even more preferred embodiment in combination with any of the above or below embodiments $R^7$ is selected from a phenyl, which is optionally substituted with 1 to 3 substituents independently selected from F, Cl, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from F, Cl, OH, Me (—CH$_3$), OMe (—O—CH$_3$), CHF$_2$, CF$_3$, OCHF$_2$, OCF$_3$.

In an even more preferred embodiment in combination with any of the above or below embodiments $R^7$ is selected from the group consisting of

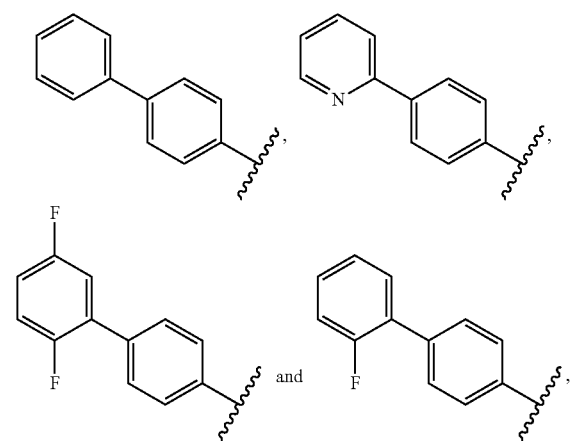

such as preferably from

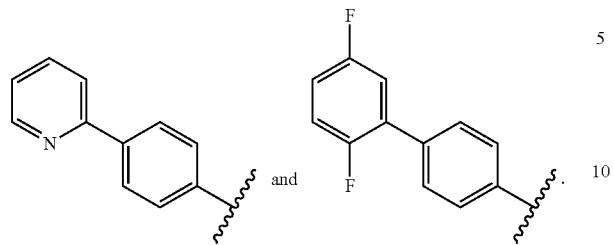
and

In yet another alternative preferred embodiment in combination with any of the above or below embodiments in Formula (I) the group

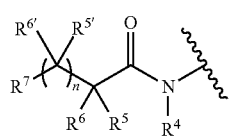

is selected from the group consisting of

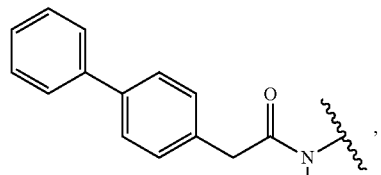,

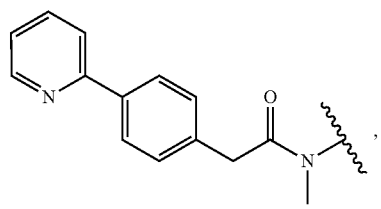,

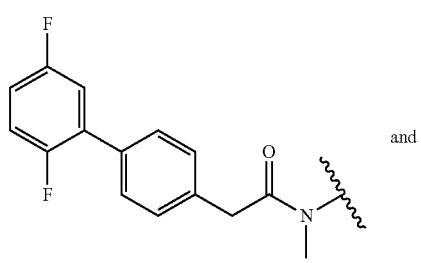 and

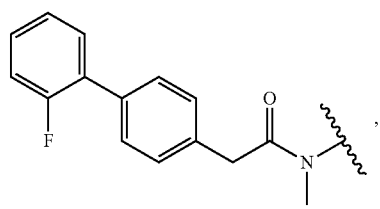, preferably from

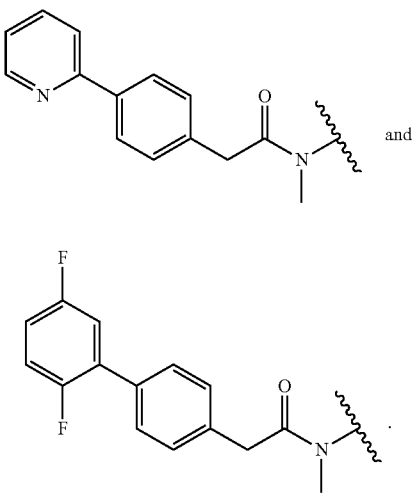 [SMILES: *N(C)C(=O)Cc1ccc(-c2ccccn2)cc1 ; *N(C)C(=O)Cc1ccc(-c2cc(F)ccc2F)cc1]
and

Preferred compounds of the present invention are also represented by the following Formulas (IIa), (IIb) and (IIc):

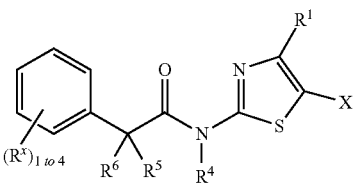

(IIa)

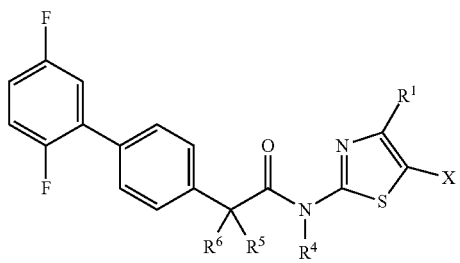

(IIb)

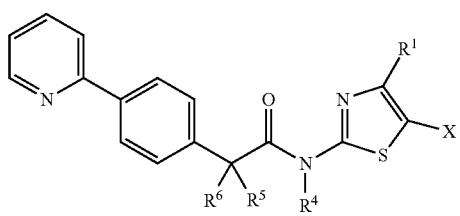

(IIc)

wherein the remaining substituents have the meaning as described in any of the embodiments described herein and wherein $R^x$ defines 1 to 4 substituents ($R^x$), which independently have the meaning as defined in any of the embodiments described herein for the possible substituents of $R^7$, preferably the 1 to 4 substituents $R^x$ are independently selected from H, F, Cl, OH, Me (—$CH_3$), OMe (—O—$CH_3$), $CHF_2$, $CF_3$, $OCHF_2$ and $OCF_3$.

In yet another alternative preferred embodiment in combination with any of the above or below embodiments in Formula (I) or (II) the group X is selected from a group consisting of

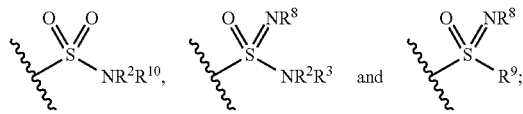

and

R$^1$ is independently selected from C$_{1-3}$-alkyl, halo-C$_{1-3}$-alkyl and cyclopropyl, more preferably R$^1$ is Me (—CH$_3$).

In yet another alternative preferred embodiment in combination with any of the above or below embodiments in Formula (I) or (II) the group X is selected from

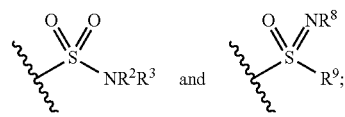

and

R$^1$ is independently selected from H, halogen, C$_{1-6}$-alkyl, halo-C$_{1-6}$-alkyl, C$_{3-6}$-cycloalkyl, halo-C$_{3-6}$-cycloalkyl, —O—C$_{1-6}$-alkyl, —O-halo-C$_{1-6}$-alkyl and —NH—C$_{1-6}$-alkyl.

In yet another alternative preferred embodiment in combination with any of the above or below embodiments R$^2$ and R$^3$ are independently selected from H, C$_{1-3}$-alkyl, halo-C$_{1-3}$-alkyl, —O—C$_{1-3}$-alkyl, —O-fluoro-C$_{1-3}$-alkyl, C$_{3-6}$-cycloalkyl and C$_{3-6}$-heterocycloalkyl, wherein alkyl, cycloalkyl and heterocycloalkyl are optionally substituted with 1 to 5 substituents independently selected from F, Cl, OH, oxo, Me (—CH$_3$), CHF$_2$ and CF$_3$;

or R$^2$ and R$^3$ when taken together with the nitrogen to which they are attached complete a 5- to 6-membered ring containing carbon atoms and optionally containing one heteroatoms selected from O, S or N, wherein the ring is unsubstituted or substituted with 1 to 4 substitutents independently selected from the group consisting of F, Cl, OH, oxo, Me (—CH$_3$), CHF$_2$ and CF$_3$;

R$^8$ is selected from H, —CN, —NO$_2$, OH, C$_{1-3}$-alkyl, fluoro-C$_{1-3}$-alkyl and O-fluoro-C$_{1-3}$-alkyl, R$^9$ is selected from C$_{1-3}$-alkyl, t-butyl, fluoro-C$_{1-3}$-alkyl, cyclopropyl, fluoro-C$_{1-3}$-alkyl-cyclopropyl, —C$_{3-10}$-heterocycloalkyl;

R$^{10}$ is selected from —CN, OH, and —NO$_2$; and

R$^{12}$ is independently selected from H, Me (—CH$_3$) and Et (—CH$_2$—CH$_3$).

Further, in any of the above or below described embodiments the substituents may individually or in any combination with each other have the following meaning:

R$^2$ and R$^3$ may independently be selected from H, Me (—CH$_3$), Et (—CH$_2$—CH$_3$), —CH$_2$CH$_2$OH and —CH$_2$CH$_2$F.

R$^2$ and R$^3$ may be H.

R$^8$ may be selected from H, —CN, —NO$_2$, OH, C$_{1-3}$-alkyl, 0-C$_{1-3}$-alkyl, fluoro-C$_{1-3}$-alkyl and O-fluoro-C$_{1-3}$-alkyl.

R$^8$ may be selected from H, —CN, —NO$_2$, OH, Me (—CH$_3$), Et (—CH$_2$—CH$_3$), OMe (—O—CH$_3$) and OEt (—O—CH$_2$—CH$_3$).

R$^8$ may be selected from H and CN.

R$^9$ may be selected from C$_{1-3}$-alkyl, fluoro-C$_{1-3}$-alkyl, cyclopropyl and —C$_{3-10}$-heterocycloalkyl.

R$^9$ may be selected from Me (—CH$_3$), Et (—CH$_2$—CH$_3$), CHF$_2$, CF$_3$, cyclopropyl and oxetane.

R$^9$ may be Me (—CH$_3$) or cyclopropyl.

R$^9$ may be Me (—CH$_3$).

R$^{10}$ may be selected from —CN, OH, and —NO$_2$.

R$^{10}$ may be —CN.

R$^{12}$ may independently be selected from H, Me (—CH$_3$) and Et (—CH$_2$—CH$_3$);

In yet another alternative preferred embodiment in combination with any of the above or below embodiments in the Formula (I) or (II) of the present invention the group

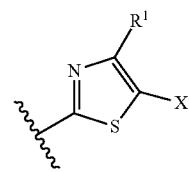

is selected from

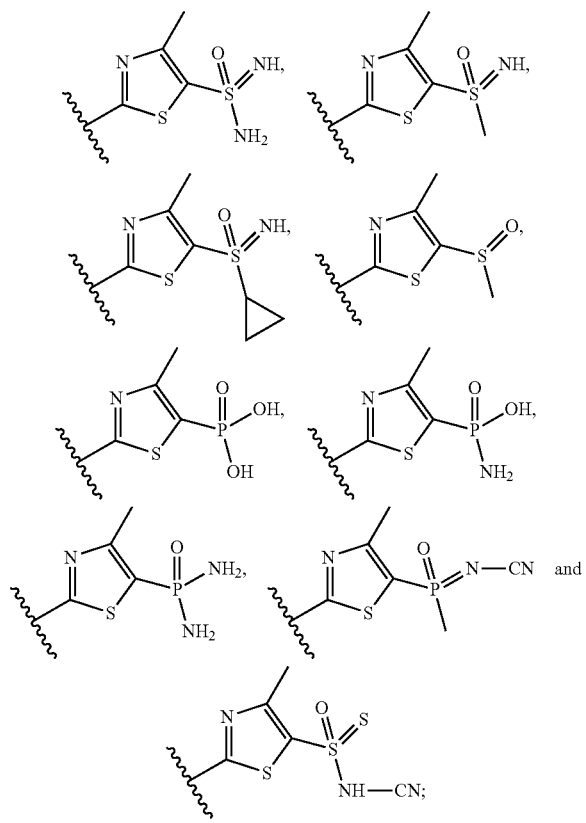

preferably said group is selected from
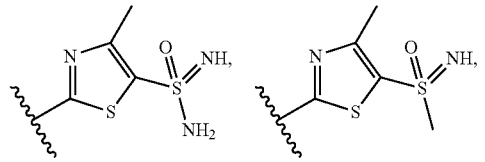
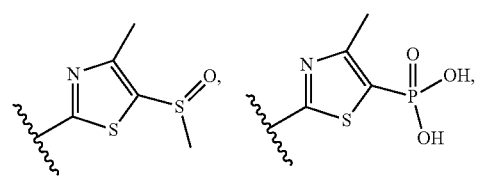
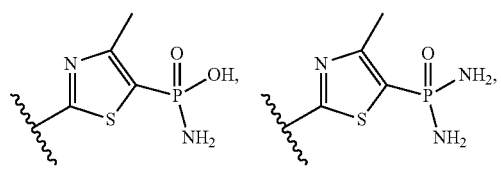
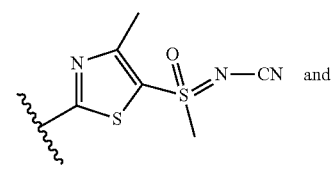
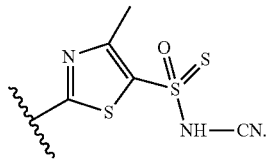
In yet another alternative preferred embodiment in combination with any of the above or below embodiments n is selected from 0 and 1, preferably n is 0.
Particularly preferred compounds of the present invention are represented by the following formulas:
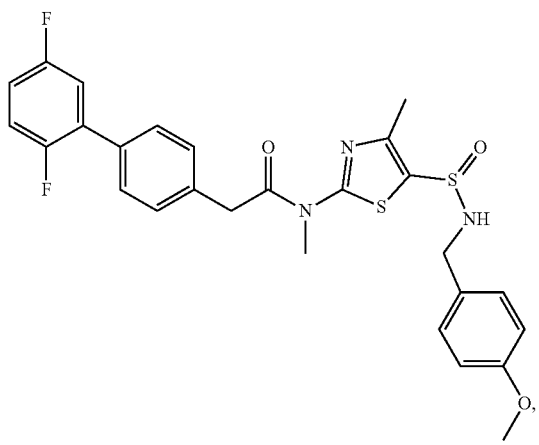
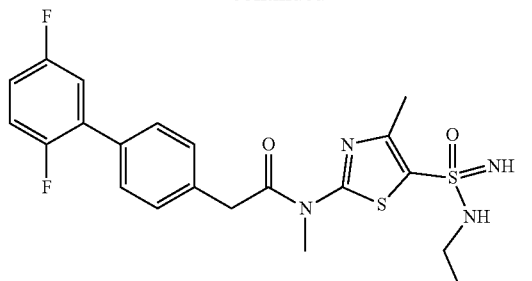
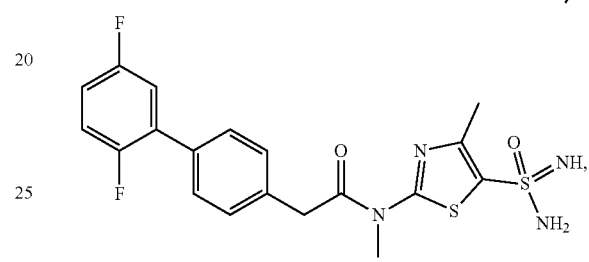
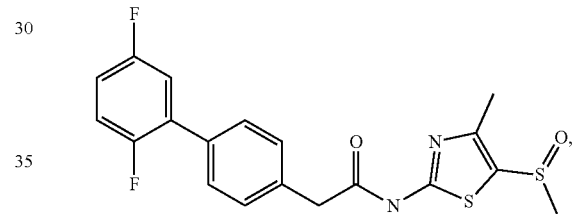
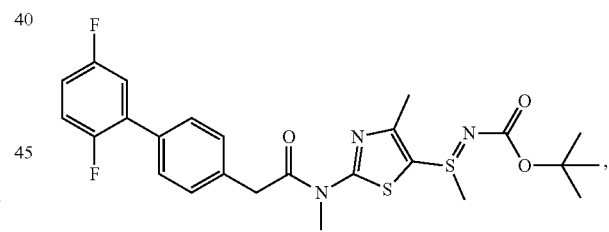
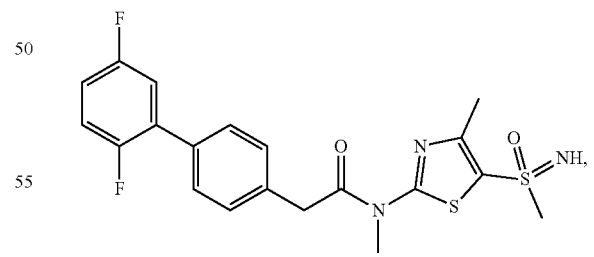
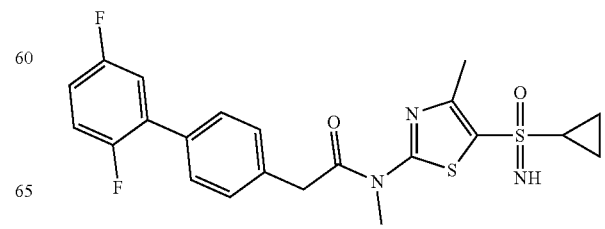

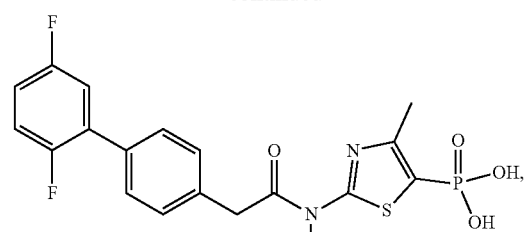
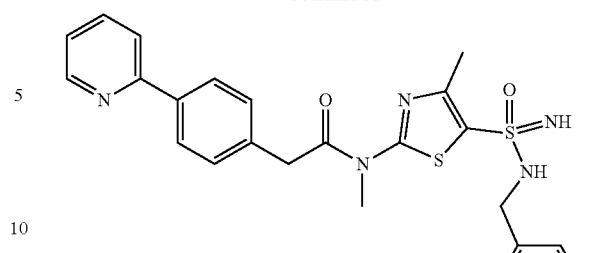
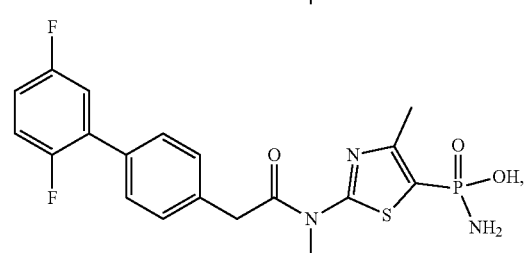
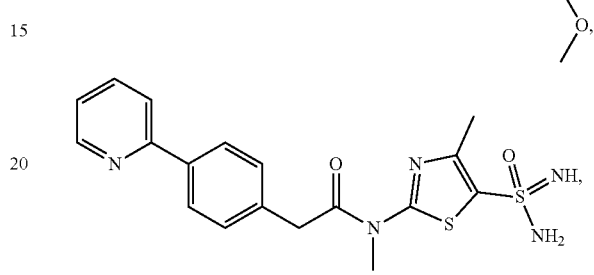
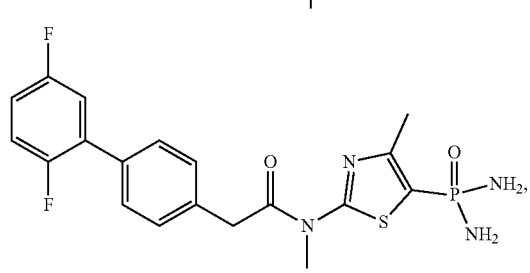
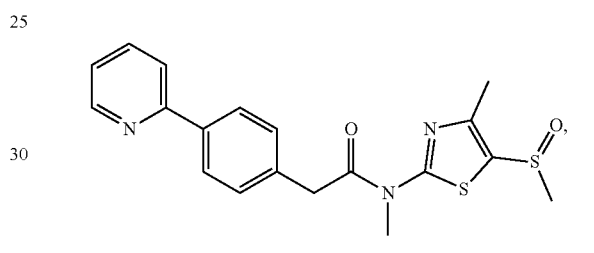
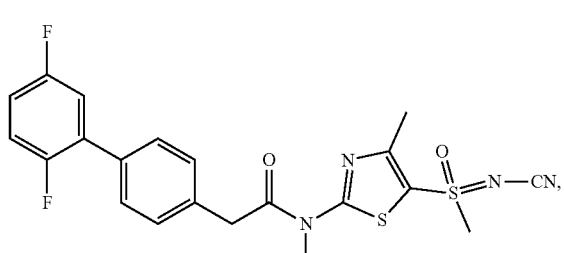
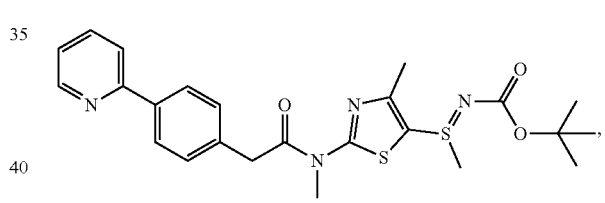
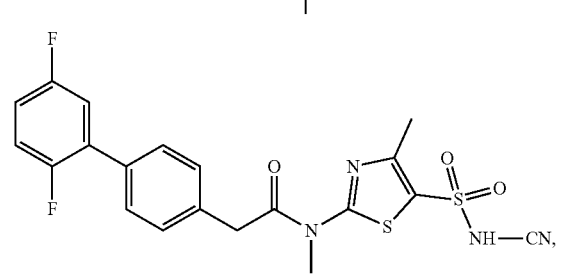
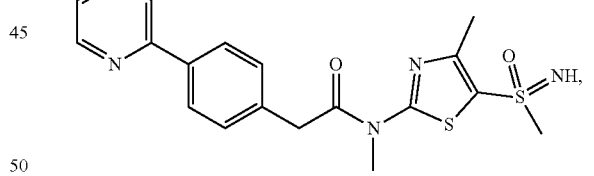
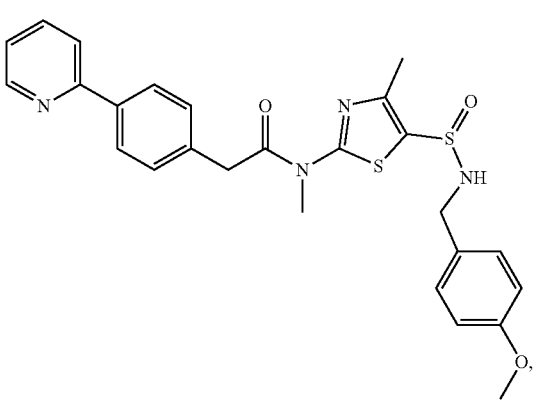
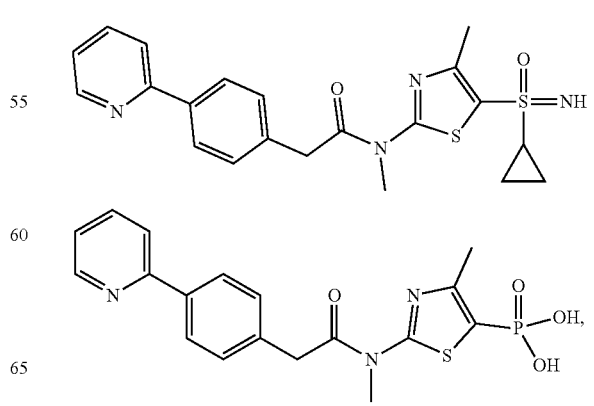

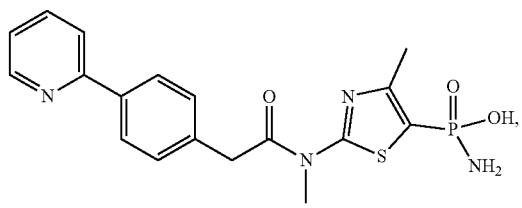
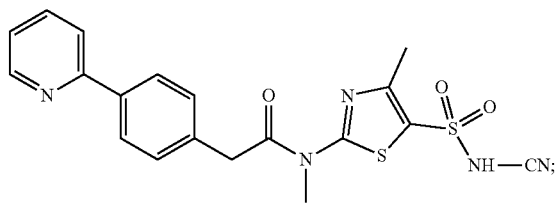
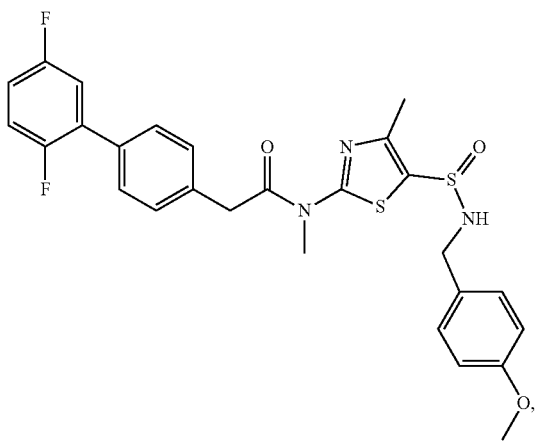
with the following compounds being preferred:
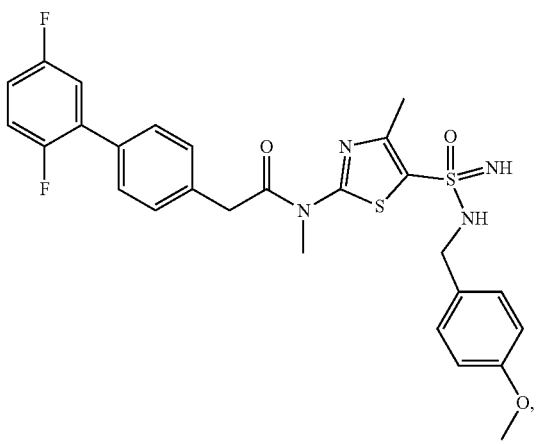
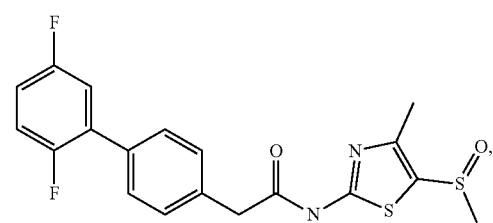
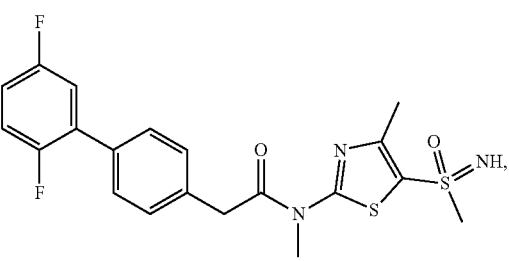
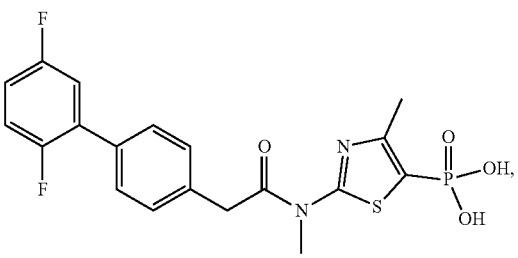

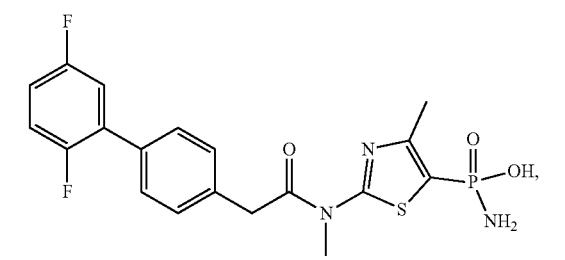
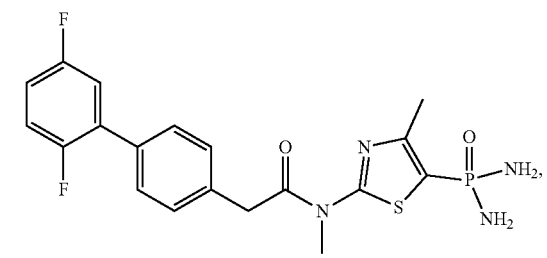
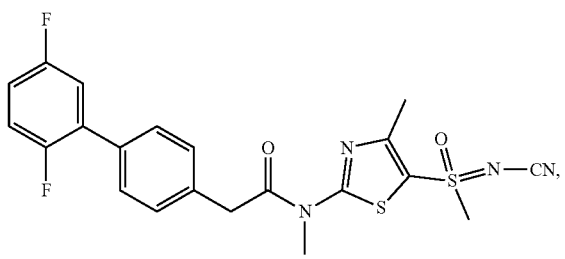
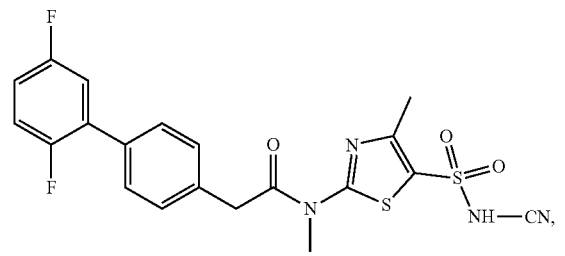
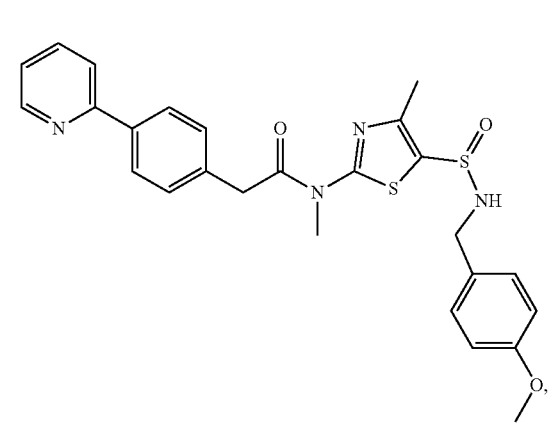
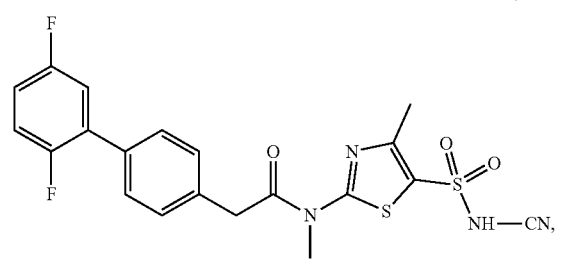
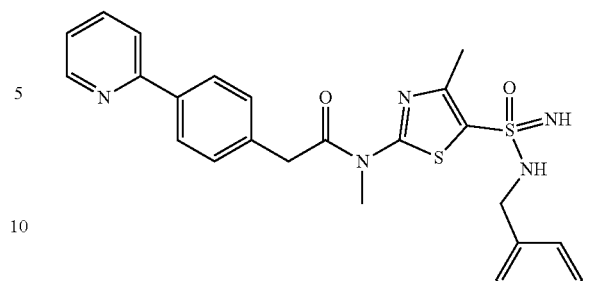
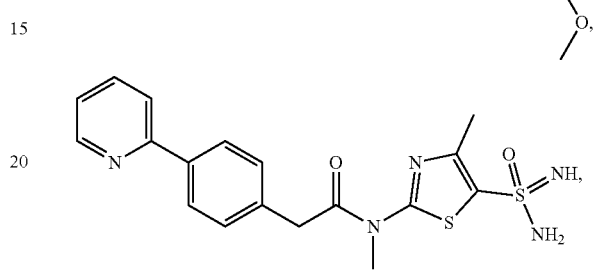
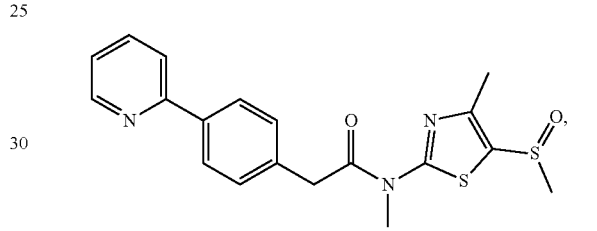
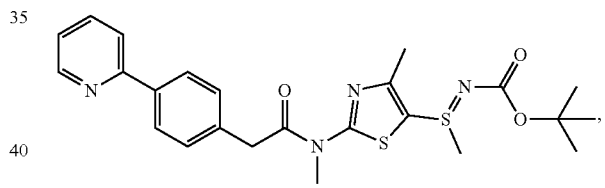
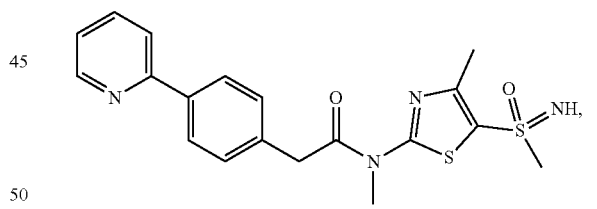
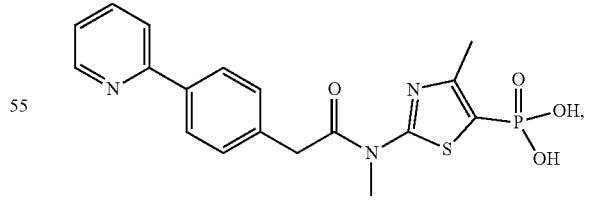
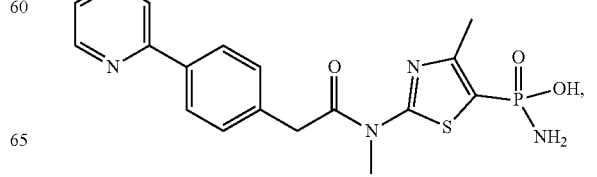

-continued

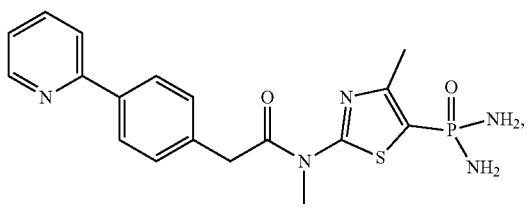

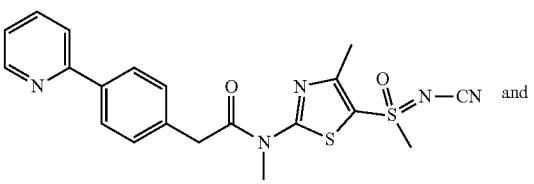

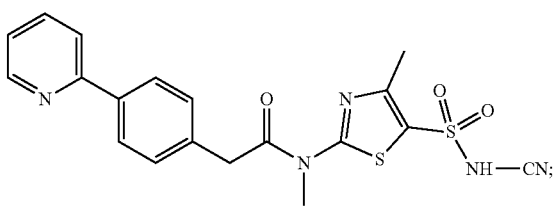

with the following compounds being more preferred:

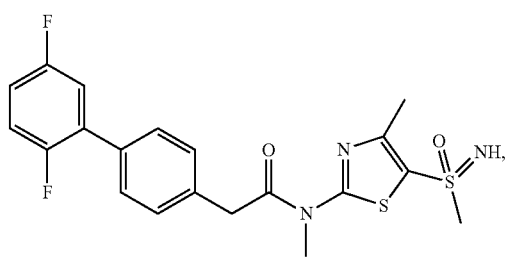

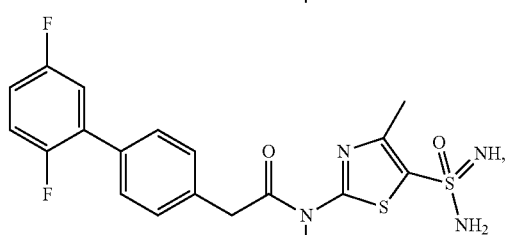

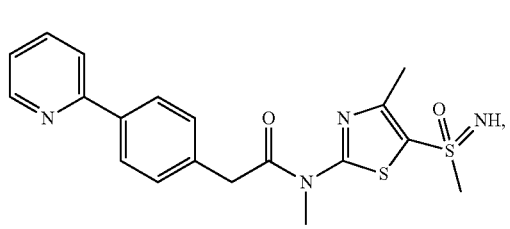

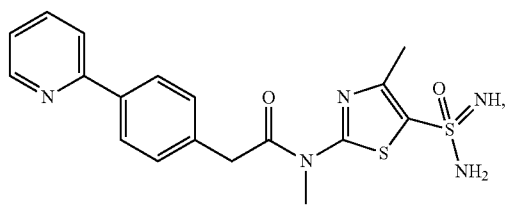

-continued

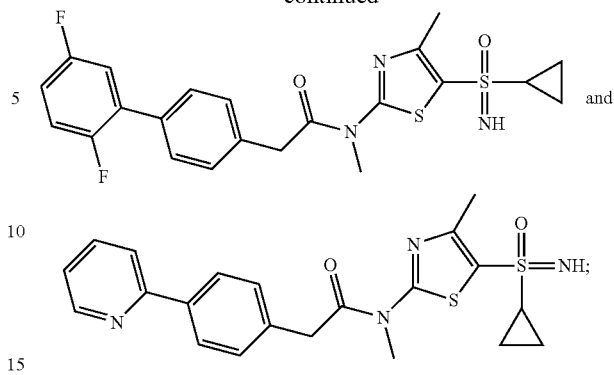

and with the following compounds being most preferred:

A further aspect of the present invention relates to the compounds of any of the above described embodiments for the use as a medicament.

Particularly the invention relates to the described compounds for use in the treatment or prophylaxis of a disease or disorder associated with viral infections.

More particularly the invention relates to the described compounds for use in the treatment or prophylaxis of a disease or disorder, which is associated with viral infections caused by herpes viruses, such as in particular by Herpes simplex viruses.

In a further aspect the inventions relates to the described compounds for use in the treatment or prophylaxis neurodegenerative diseases caused by viruses, such as in particular Alzheimers disease.

In a further aspect the inventions relates to the described compounds for the use in the treatment and prophylaxis of herpes infections, in particular Herpes simplex infections in patients displaying Herpes labialis, Herpes genitalis and Herpes-related keratitis, Alzheimers disease, encephalitis, pneumonia, hepatitis; in patients with a suppressed immune system, such as AIDS patients, cancer patients, patients having a genetic immunodeficiency, transplant patients; in new-born children and infants; in Herpes-positive patients, in particular Herpes-simplex-positive patients, for suppressing recurrence (suppression therapy); patients, in particular in Herpes-positive patients, in particular Herpes-simplex-positive patients, who are resistant to nucleosidic antiviral therapy such as acyclovir, penciclovir, famciclovir, ganciclovir, valacyclovir.

In a further aspect the inventions relates to the described compounds, which are characterized by an $IC_{50}$ value (HSV-1/Vero) in an in vitro activity selectivity assay HSV-1 on Vero cells as described in the Examples of the present invention of preferably $IC_{50}$ below 100 µM, more preferably $IC_{50}$ below 10 µM and very particularly preferable $IC_{50}$ below 1 µM.

In a further aspect the inventions relates to the described compounds, which are characterized by an $ED_{50}$ value in an in vivo animal model as described in the Examples of the present invention preferably of $ED_{50}$ of less than 10 mg/kg for HSV-1, more preferably of less than 5 mg/kg for HSV-1, and very particularly preferable of less than 2 mg/kg for HSV-1.

In a further aspect the inventions relates to the described compounds, which are characterized by showing no or reduced carbonic anhydrase inhibition, such particularly inhibition of carbonic anhydrase I and/or carbonic anhydrase II. In the sense of the present invention no or reduced carbonic anhydrase inhibition is particularly defined by $IC_{50}$-values (inhibitory concentration) in a carbonic anhydrase II activity assay according to R. Iyer et al. *J. Biomol. Screen.* 2006, 11:782 and/or in a carbonic anhydrase I activity assay according to A. R. Katritzky et al. *J. Med. Chem.* 1987, 30:2058 of $IC_{50}$>2.0 µM, preferably >3.0 µM, more preferably >5.0 µM. Even more preferably, no or reduced carbonic anhydrase inhibition in the sense of the present invention is particularly defined by $IC_{50}$-values (inhibitory concentration) in a human carbonic anhydrase II activity assay as described in detail in the Examples of the present invention of $IC_{50}$>2.0 µM, preferably >3.0 µM, more preferably >5.0 µM.

The compound according to the present invention are considered for the use in the prophylaxis and treatment of the respective disorders and diseases in humans as well as in animals.

Accordingly, the invention relates to the use of the compounds as described herein for the preparation of a medicament.

Further, the invention relates to a method of treating a disease or disorder associated with viral infections, such as a disease or disorder, which is associated with viral infections caused by herpes viruses, such as in particular by Herpes simplex viruses as well as a method of treating neurodegenerative diseases caused by viruses, such as in particular Alzheimers disease, said methods comprising administering to a human or animal in need thereof an effective amount of a compound or of a composition comprising said compounds as described herein.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray or as eye drops.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally or as eye drops, more preferably the compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

The compounds of the present invention may also be present in combination with further active ingredients, in particular with one or more active ingredients exhibiting advantageous effects in the treatment of any of the disorders or diseases as described herein. Very particularly the compounds of the present invention are present in a composition in combination with at least one further active substance being effective in treating a disease or disorder associated with viral infections (antiviral active compounds), preferably a disease or disorder being associated with viral infections caused by herpes viruses, such as in particular by Herpes simplex viruses, thus relating to a so called combination therapy. The at least one further active substance being effective in treating a disease or disorder associated with viral infections (antiviral active compounds) are preferably selected from the group consisting of nucleosidic drugs such as acyclovir, valacyclovir, penciclovir, ganciclovir, famciclovir and trifluridine, as well as compounds such as foscarnet and cidofovir.

Accordingly, the present invention further relates to a pharmaceutical composition comprising one or more of the compounds as described herein and at least one pharmaceutically acceptable carrier and/or excipient and/or at least one further active substance being effective in treating a disease or disorder associated with viral infections (antiviral active compounds).

EXPERIMENTAL PART

The compounds of the present invention can be prepared by a combination of methods known in the art including the procedures described in Schemes I to III below.

The synthesis of the acid building block $R^7(CR^{5'}R^{6'})_nCR^5R^6COOH$ can be made as described in WO2001/47904 and coupled to the appropriate thiazole building block. To install a dialkyl phosphonate Ia, the 5-unsubstituted thiazole (X=H) can be treated with $Mn(OAc)_3 \cdot 2H_2O$ and dialkyl phosphite. The dialkyl phosphonate Ia can get saponified using e.g. TMSBr to afford phosphonic acid Ib as depicted in Scheme I. Preparation of the phosphonamides can be accomplished by treating the phosphonic acid Ib with oxalyl chloride and then with an appropriate amount of ammonia ($R^2$ and $R^3$=H), primary and secondary amines. After chromatographic separation target compound Ic and Id can get separated. The introduction of appropriate substituted sulfonamides ($X=SO_2NR^2R^{10}$) can be obtained by either alkylating the known primary sulfonamide ($X=SO_2NH_2$) with halogenide-$R^{10}$ (e.g. bromocyan) or reacting the known sulfonic acid chloride intermediate ($X=SO_2Cl$) with an appropriate amine (e.g. $NH_2OH$, $NH_2CN$).

Scheme I

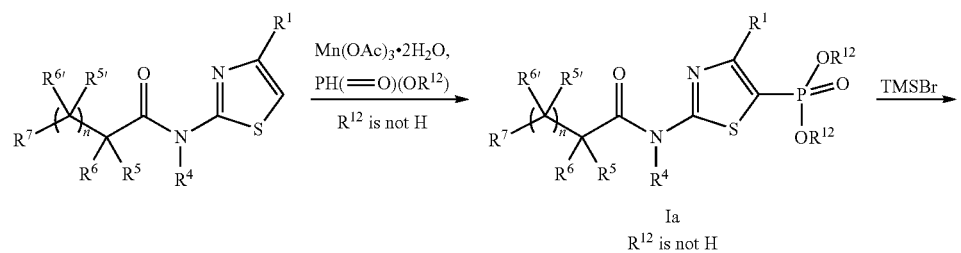

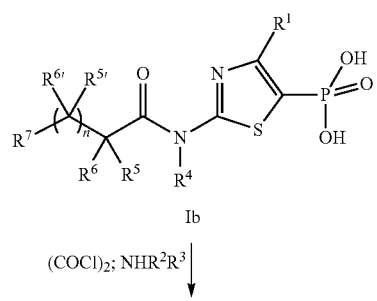

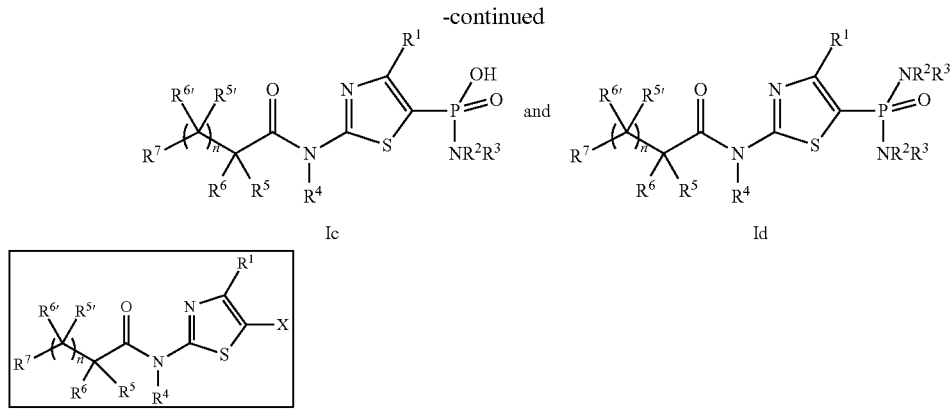

Coupling of acid building block R[7](CR[5']R[6'])$_n$CR[5]R[6]COOH with 5-sulfonic acid-substituted thiazole can afford intermediate IIa (Scheme II), which can be converted to sulfonyl chloride IIa by treating with oxalyl chloride. Reaction of this intermediate with NHR[2]R[3] and triphenylphosphine give target compound 11c, which finally can be oxidized e.g. with tert-butylhypo chlorite in presence of NH$_2$R[8] to furnish target compound IId. An alternative route towards derivatives IId using readily available sulfonamides is described by Y. Chen et al. (RSC Advances 2015, 5, 4171) through nucleophilic substitution of sulfonimidoyl chloride formed in situ with different amines. Additional routes for derivatives Iid are described in Angew. Chem. Int. Ed. 2013, 52, 9399 and ChemMedChem 2013, 8, 1067.

Scheme II

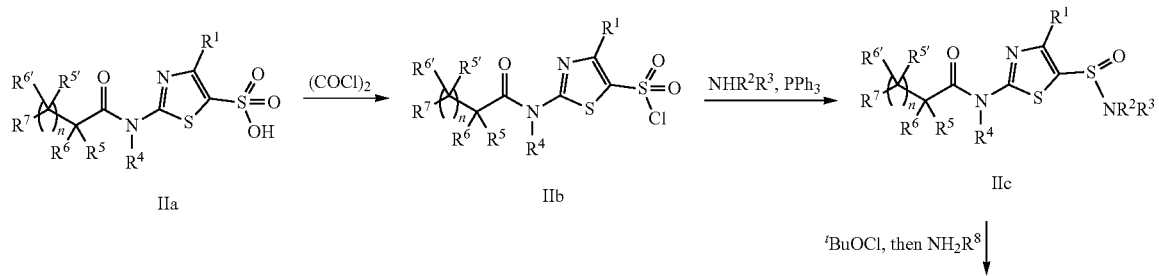

Coupling of acid building block $R^7(CR^{5'}R^{6'})_nCR^5R^6COOH$ with 5-alkylthio-substituted thiazole can afford intermediate IIIa (Scheme III), which can get oxidized to the alkylsulfinyl derivative IIIb. Also, oxidation of intermediate IIIa with azido derivative $N_3R^8$ and $FeCl_2$ can furnish sulfinimidoyl derivative IIIc, which can further get oxidized, e.g. with $NaIO_4/RuCl_3$ to afford sulfonimidoyl derivative IIId. In case $R^8$ represents a cyano residue, an alternative route as outlined by S. J. Park et al. (ChemMedChem 2013, 8, 217) can also be used ($H_2NCN$, $PhI(OAc)_2$, then mCPBA).

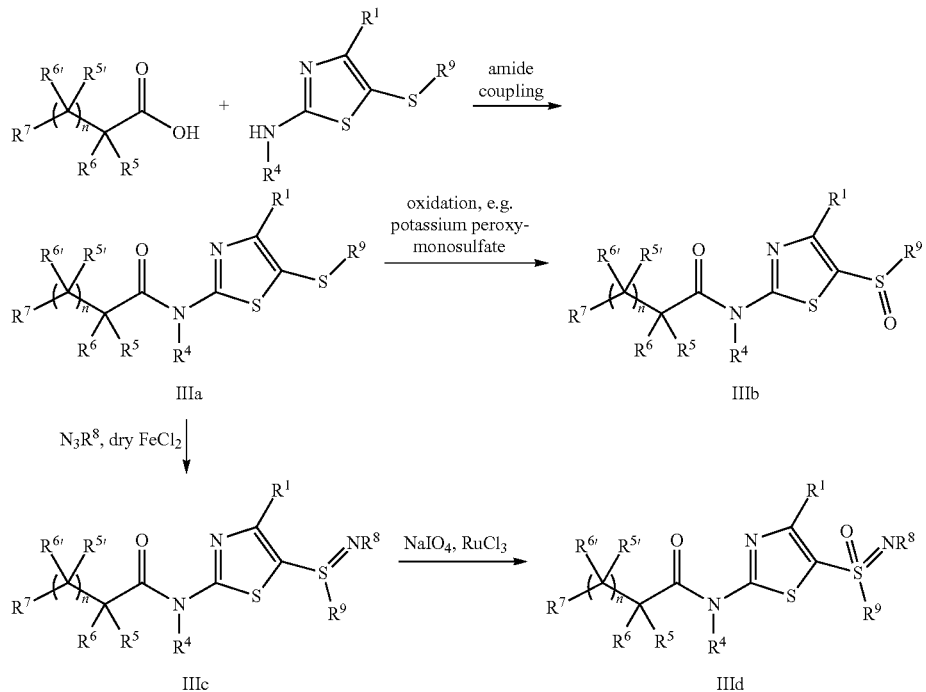

Scheme III

In all cases $R^2$, $R^3$ or $R^8$ may serve as a protecting group and can get deprotected similar as described in e.g. Greene's Protective Groups in Organic Synthesis (ISBN: 978-1-118-05748-3).

In the reaction schemes the remaining substituents may have the meaning as defined in the present invention.

Abbreviations

HPMC hydroxypropylmethylcellulose

DMF dimethylformamide

DCM dichloromethane

THF tetrahydrofurane

PE petroleum ether

DMSO dimethylsulfoxide

HATU 1-[bis(dimethylamino)methylene]-1H-1,2,3-triazolo[4,5-b]pyridinium 3-oxid hexafluorophosphate rt room temperature TFA trifluoroacetic acid TMS trimethylsilyl EDC.HCl 1-(3-dimethylaminopropyl)-3-ethylcarbodiimide hydrochloride TBDMSCl tert-butyldimethylsilyl chloride

EXPERIMENTAL SECTION

Example 1: 2-(2',5'-Difluoro-[1,1'-biphenyl]-4-yl)-N-(5-(N-(4-methoxybenzyl)sulfinamoyl)-4-methyl-thiazol-2-yl)-N-methylacetamide

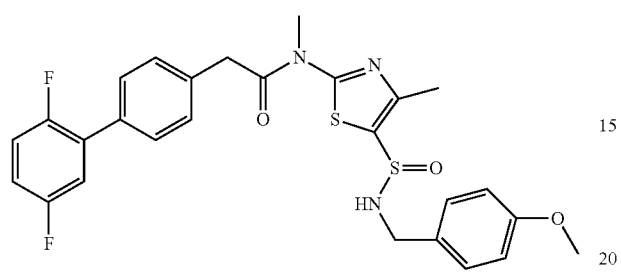

Step 1: 4-Methyl-2-methylamino-thiazole-5-sulfonic acid (P1a)

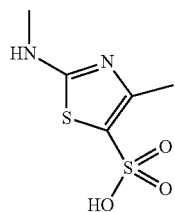

Methyl-(4-methyl-thiazol-2-yl)-amine (3.84 g, 30 mmol) was added to chlorosulfonic acid (6.0 mL, 90 mmol) under ice cooling. The mixture was stirred overnight, poured into ice, neutralised with 6N NaOH and evaporated to dryness. The residue was extracted with hot EtOH and the obtained extract was concentrated to dryness to afford intermediate P1a (2.73 g, 44%).

Step 2: 2-(2-(2',5'-Difluoro-[1,1'-biphenyl]-4-yl)-N-methylacetamido)-4-methylthiazole-5-sulfonic acid (P1b)

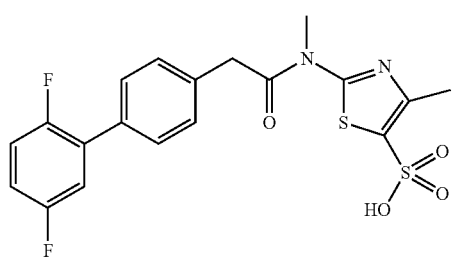

A solution of sulfonic acid P1a (2.73 g, 13 mmol) and N-methylmorpholine (3.3 mL, 30 mmol) in DMF (5 mL) was cooled to 0° C. and an ice-cold solution of 2-(2',5'-difluoro-[1,1'-biphenyl]-4-yl)acetic acid (2.48 g, 10 mmol; WO 2003/000259), EDC.HCl (2.11 g, 11 mmol) and HOBt (1.49 g, 11 mmol) in DMF (7 mL) was added. The mixture was allowed to reach rt, stirred overnight and poured into $Et_2O$. The precipitate was centrifuged and washed with $Et_2O$, diluted with few THF and cooled overnight. The precipitate P1b was centrifuged and used without further purification.

Step 3: 2-(2-(2',5'-Difluoro-[1,1'-biphenyl]-4-yl)-N-methylacetamido)-4-methylthiazole-5-sulfonyl chloride (P1c)

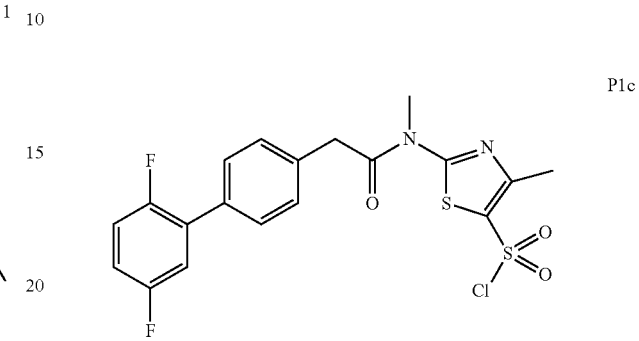

A suspension of sulfonic acid P1b (374 mg, 854 µmol) in dry THF (5 mL) was stirred over molecular sieves for 1 h, then the molecular sieves were removed and the solution was cooled to −20° C. Then oxalyl chloride (220 µL, 2.56 mmol) and 2 drops of DMF were added. The mixture was stirred at rt for 2 h, then additional oxalyl chloride (220 µL, 2.56 mmol) and 1 drop of DMF were added. The mixture was stirred at 60° C. for 2 h, concentrated dissolved it EtOAc and washed with aq. $KH_2PO_4$-solution (1M) and brine, dried over $Na_2SO_4$ and evaporated to afford intermediate P1c (167 mg, 43%).

Step 4: 2-(2',5'-Difluoro-[1,1'-biphenyl]-4-yl)-N-(5-(N-(4-methoxybenzyl)sulfinamoyl)-4-methylthiazol-2-yl)-N-methylacetamide (1)

A solution of sulfonyl chloride P1c (167 mg, 366 µmol) in DCM (2.5 mL) was cooled to −20° C., then $NEt_3$ (102 µL, 732 µmol) and a cooled solution of $PPh_3$ (86 mg, 329 µmol) and p-methoxybenzyl amine (72 µL, 549 µmol) in DCM (0.8 mL) was added. The mixture was stirred for 15 min at 0° C. and 1 h at rt and then diluted with PE (40 mL). The precipitate was dissolved in DCM (2 mL) and precipitated again from $Et_2O$ (25 mL). The supernatant was concentrated to dryness and the residue was used without further purification. MS found: 542.3 $[M+H]^+$.

Example 2: 2-[4-(2,5-Difluorophenyl)phenyl]-N-[5-[[(4-methoxybenzyl)amino]sulfonimidoyl]-4-methyl-thiazol-2-yl]-N-methyl-acetamide

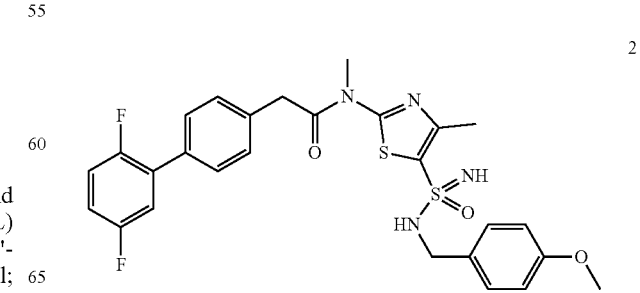

A solution of compound 1 (approx. 90 μmol) in dry THF (1.5 mL) was cooled to −20° C. Then tert-butylhypo chlorite in dry THF (100 μL) was added and the solution was stirred for 30 min at 0° C., quenched with NH$_3$ (0.5M in THF; 810 μL, 405 μmol), stirred for 1 h at 0° C. and precipitated from PE (30 ml). The crude product 2 was used without further purification in the next step.

Example 3: 2-(2',5'-Difluoro-[1,1'-biphenyl]-4-yl)-N-methyl-N-(4-methyl-5-sulfamimidoylthiazol-2-yl) acetamide

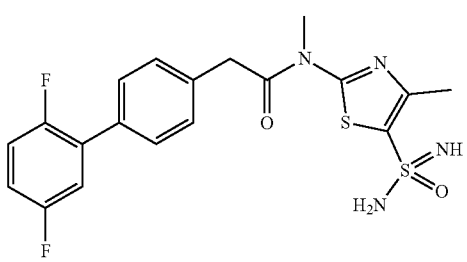

3

To a solution of p-methoxybenzylsulfonimidamide 2 (approx. 40 μmol) in MeCN (0.5 mL) was added a solution of cer(IV) ammonium nitrate (110 mg, 200 μmol) in water (100 μL) and the solution was stirred at rt for 10 min. The organic layer was separated and the aqueous layer was extracted again with MeCN. The combined organic layers were diluted with water to a mixture of MeCN/H$_2$O=7:1 and purified by HPLC to obtain the target molecule 3. $^1$H-NMR (CDCl$_3$+CD$_3$OD, 300 MHz) δ: 7.58-7.54 (m, 3H), 7.37 (d, 2H), 7.17-7.06 (m, 3H), 4.17 (s, 2H), 3.79 (s, 3H), 2.63 (s, 3H). MS found: 437 [M+H]$^+$.
Alternatively, Example 3 can be prepared as follows:

Step 1: N-(5-(N-(tert-Butyldimethylsilyl)sulfamoyl)-4-methylthiazol-2-yl)-2-(2',5'-difluoro-[1,1'-biphenyl]-4-yl)-N-methylacetamide (3a)

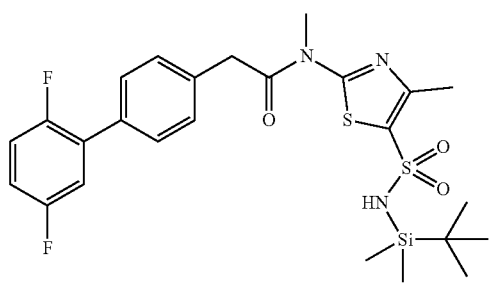

3a

To a solution of 2-(2',5'-difluoro-[1,1-biphenyl]-4-yl)-N-methyl-N-(4-methyl-5-sulfamoylthiazol-2-yl)acetamide (250 mg, 572 μmol; prepared as described in WO2001/47904) in DMF (3 mL) was added NaH (1.14 mmol, 46 mg; 60% suspension in mineral oil) and the mixture was stirred for 1 h at rt. After addition of TEA (2.86 mmol, 399 μL) the mixture was cooled to −20° C. and a cooled (−20° C.) solution of TBDMSCl (2.86 mmol, 429 mg) in dry THF (1 mL) was added and stirring was continued for 60 h at rt. The mixture was poured into water and extracted twice with EtOAc. The combined organic phases were washed twice with water, twice with sat. aq. NaHCO$_3$, once with brine, dried over Na$_2$SO$_4$, filtered and concentrated to dryness. The crude intermediate 3a was used in the next step without further purification.

Step 2: 2-(2',5-Difluoro-biphenyl-4-yl)-N-[5-sulfinimidamido-4-methyl-thiazol-2-yl]-N-methyl acetamide (Example 3)

To a solution of intermediate 3a (ca. 286 μmol) in DCM (3 mL) was added TEA (1.43 mmol, 200 μL) and the mixture was cooled to −20° C. Then a cooled (−20° C.) solution of triphenylphosphinedichloride (572 μmol, 191 mg) in DCM (600 μL) was added. Stirring was continued for 2.5 h at rt and the mixture was poured into a mixture of 25% NH$_3$ (aq.) and THF (1:2, v/v, 30 mL) under cooling with ice. The organic phase was separated and diluted with EtOAc. The aqueous phase was extracted with EtOAc and the organic phases were combined, washed with water, twice with 1M KHSO$_4$, once with brine, dried over Na$_2$SO$_4$, filtered and concentrated to dryness. The crude product was dissolved in DCM (1 mL) and precipitated with PE. The obtained precipitate was dissolved in DCM (1 mL) and precipitated with Et$_2$O to obtain the target molecule 3 (79 mg, 50% over both steps).

Example 3-1: N-methyl-N-(4-methyl-5-sulfamimdoylthiazol-2-yl)-2-(4-(pyridin-2-yl)phenyl)acetamide

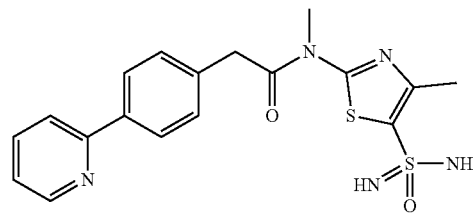

3-1

Example 3-1 was prepared according to the protocol used to synthesize Example 3 using (4-pyridin-2-yl-phenyl)acetic acid. $^1$H-NMR (CDCl$_3$+CD$_3$OD, 300 MHz) δ: 8.68-8.67 (s, 1H), 8.06-8.04 (s, 1H), 7.95-7.93 (m, 3H), 7.67-7.46 (m, 4H), 4.24 (s, 2H), 3.83 (s, 3H), 2.65 (s, 3H). MS found: 402 [M+H]$^+$, 201, 5 [M+2H]$^{2+}$.

Example 4: 2-(2',5'-Difluoro-[1,1'-biphenyl]-4-yl)-N-methyl-N-(4-methyl-5-(methylsulfinyl) thiazol-2-yl)acetamide

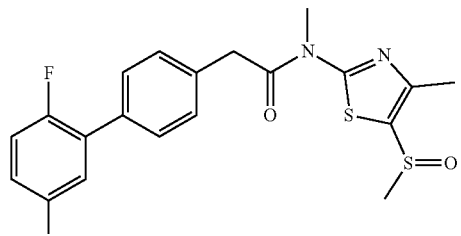

4

Step 1: N,4-Dimethyl-5-(methylthio)thiazol-2-amine (P4a)

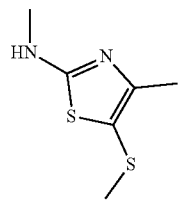

To a solution of 5-bromo-N,4-dimethylthiazol-2-amine (2.06 g, 9.95 mmol) in MeOH (20 mL) was slowly added under ice cooling a solution of NaSMe (1.74 g, 24.9 mmol) in MeOH (15 mL). The mixture was heated to 60° C. and stirred for 2 h, evaporated and suspended in MeCN. After centrifugation, the supernatant was separated and evaporated. The obtained solid was slurried with Et$_2$O and centrifuged to give intermediate P4a.

Further compounds can be prepared by using NaS—Z, wherein Z belongs to a group of $C_{1-3}$-alkyl, t-butyl, cyclopropyl, fluoro-$C_{1-3}$-alkyl-cyclopropyl, —$C_{3-10}$-heterocycloalkyl.

Step 2: 2-(2',5'-Difluoro-[1,1'-biphenyl]-4-yl)-N-methyl-N-(4-methyl-5-(methylthio)thiazol-2-yl)acetamide (P4b)

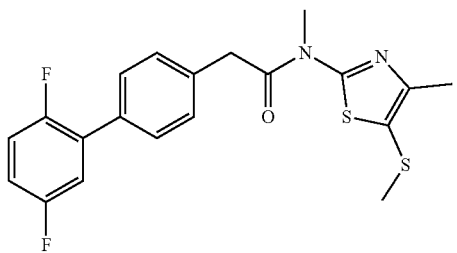

A solution of amine P4a (994 mg; 5.71 mmol) and DIPEA (1.89 mL, 11.4 mmol) in DMF (3 mL) was cooled to −20° C., then a cooled solution of 2-(2',5'-difluoro-[1,1'-biphenyl]-4-yl)acetic acid (1.56 g, 6.28 mmol; WO 2003/000259) and HATU (2.39 g, 6.28 mmol) in DMF (5 mL) was added and the mixture was stirred at rt overnight, poured into water and extracted with EtOAc (2×). The combined organic layer was washed with brine (2×) and a saturated solution of NaHCO$_3$, dried over Na$_2$SO$_4$, evaporated and purified by column chromatography (PE/DCM=1:0 to 1:1) to afford intermediate P4b (625 mg, 27%).

Step 3: 2-(2'',5''-Difluoro-[1,1'-biphenyl]-4-yl)-N-methyl-N-(4-methyl-5-(methylsulfinyl)thiazol-2-yl)acetamide (4)

A solution of intermediate P4b (1.4 g, 3.46 mmol) in MeOH (35 mL) was cooled to 0° C., then potassium peroxymonosulfate (1.09 g, 1.77 mmol) in water (18 mL) was added and the solution was stirred for 20 min at 0° C., quenched with a saturated Na$_2$S$_2$O$_3$-solution and extracted with EtOAc (2×). The combined organic layer was washed with water (2×) and brine, dried over Na$_2$SO$_4$, evaporated and purified by column chromatography (PE/DCM/MeOH=1:0:0 to 1:1:0 to 0:19:1) to afford the target compound 4 (419 mg, 29%). $^1$H-NMR (CDCl$_3$, 250 MHz) δ: 7.57-7.53 (m, 2H), 7.37 (d, 2H), 7.17-6.98 (m, 3H), 4.09 (s, 2H), 3.75 (s, 3H), 2.96 (s, 3H), 2.51 (s, 3H). MS found: 421.3 [M+H]$^+$, 841.5 [2M+1-1]$^+$.

Example 5: 2-(2α,5'-Difluoro-[1,1'-biphenyl]-4-yl)-N-methyl-N-(4-methyl-5-(S-methyl-N-((1,1-dimethylethoxy)carbonyl)sulfinimidoyl)thiazol-2-yl)acetamide

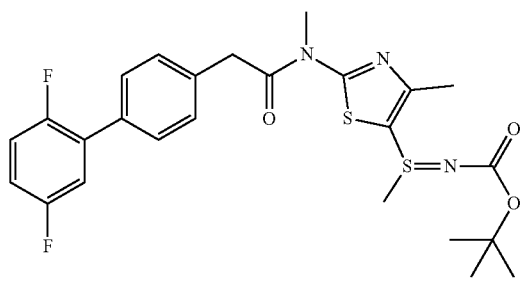

A solution of compound P4b (197 mg, 390 μmol) and tert-butyl azidoformate (277 mg, 1.95 mmol) in dry, degassed DCM (1.5 mL) was cooled to −20° C. under argon. Then anhydrous FeCl$_2$ (49 mg, 390 μmol) was added and the solution was allowed to reach rt and stirred for 4 h, diluted with water and extracted with EtOAc (2×). The combined organic layer was washed with water and brine, dried over Na$_2$SO$_4$ and evaporated to afford target compound 5. MS found: 520.4 [M+H]$^+$.

Example 6: 2-(2',5'-Difluoro-[1,1'-biphenyl]-4-yl)-N-methyl-(4-methyl-5-(S-methyl-N-((1,1-dimethylethoxy)carbonyl)sulfonimidoyl)thiazol-2-yl)acetamide

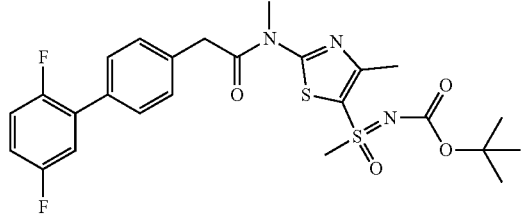

To a solution of compound 5 (100 mg, 193 μmol) in THF (10 mL) was added a solution of NaIO$_4$ (206 mg, 963 μmol) in water (3 mL) and ruthenium(III) chloride hydrate in water (330 μL). After 5 min the mixture was diluted with water and EtOAc and extracted with EtOAc (3×). The combined organic layer was washed with water and brine, dried over Na$_2$SO$_4$, evaporated and purified by HPLC to afford target compound 6.

Example 7: 2-(2',5'-Difluoro-[1,1'-biphenyl]-4-yl)-N-methyl-N-(4-methyl-5-(S-methylsulfonimidoyl)thiazol-2-yl)acetamide

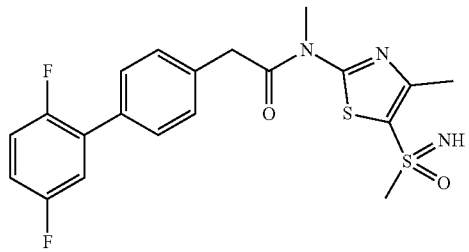

To a solution of compound 6 in DCM was added 50% aq. TFA at −20° C. and the mixture was stirred for 1 h at rt, evaporated and lyophilized from tert-BuOH/H$_2$O (4:1) to obtain target compound 7. $^1$H-NMR (CDCl$_3$, 400 MHz) δ: 7.56-7.53 (m, 2H), 7.36 (d, 2H), 7.18-6.95 (m, 3H), 4.08 (s, 2H), 3.75 (s, 3H), 2.95 (s, 3H), 2.51 (s, 3H). MS found: 436.3 [MαH]$^+$.

Example 7a: N-[5-(cyclopropylsulfonimidoyl)-4-methyl-thiazol-2-yl]-2-[4-(2,5-difluorophenyl)phenyl]-N-methyl-acetamide In a similar method an Example compound 7a can be prepared, using NaS—Z, with Z being cyclopropyl:

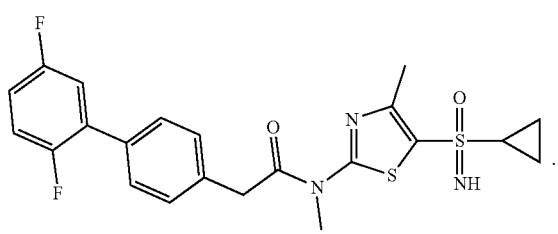

Example 7b: N-[5-(Cyclopropylsulfonimidoyl)-4-methyl-thiazol-2-yl]-N-methyl-2-[4-(2-pyridyl)phenyl]acetamide

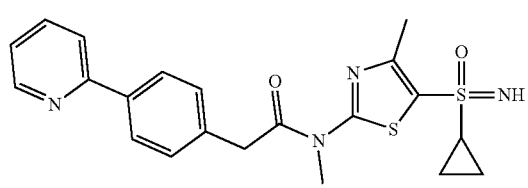

Example 7b can be prepared similar as described for Example 7a using the appropriate building blocks.

Example 8: Dimethyl (2-(2-(2',5'-difluoro-[1,1'-biphenyl]-4-yl)-N-methylacetamido)-4-methylthiazol-5-yl)phosphonate

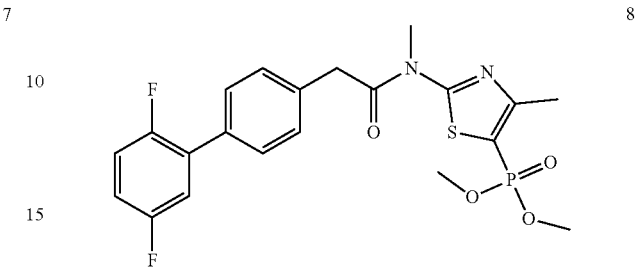

Step 1: 2-(2',5'-Difluoro-[1,1'-biphenyl]-4-yl)-N-methyl-N-(4-methylthiazol-24)acetamide (P8a)

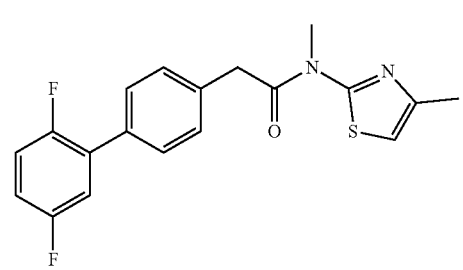

A solution of 2-(2',5'-difluoro-[1,1'-biphenyl]-4-yl)acetic acid (648 mg, 2.61 mmol; WO 2003/000259), EDC.HCl (510 mg, 2.61 mmol) and HOBt (320 mg, 2.37 mmol) in DMF (1.6 mL) was cooled to 0° C., then a cooled solution of N,4-dimethylthiazol-2-amine (304 mg, 2.37 mmol) and N-methylmorpholine (235 µL, 2.61 mmol) in DMF (1.6 mL) was added. The mixture was allowed to reach rt and stirred overnight, poured into water and extracted with EtOAc (3×). The combined organic layer was washed with a saturated solution of NaHCO$_3$ and brine, dried over Na$_2$SO$_4$ and evaporated to afford intermediate P8a (677 mg, 72%).

Step 2: Dimethyl (2-(2-(2',5'-difluoro-[1,1'-biphenyl]-4-yl)-N-methylacetamido)-4-methylthiazol-5-yl)phosphonate (8)

To a solution of intermediate P8a (670 mg, 1.85 mmol) in glacial acetic acid (25 mL) was added Mn(OAc)$_3$.2H$_2$O (1.49 g, 5.55 mmol) and the mixture was heated to 80° C. Then dimethyl phosphite (327 µL, 2.78 mmol) was added. After 1.5 additional Mn(OAc)$_3$.2H$_2$O (0.75 g) and dimethyl phosphite (218 µL) were added. After 1.5 h the mixture was cooled, poured into water and extracted with EtOAc (2×). The combined organic layer was washed with water, a saturated solution of NaHCO$_3$ (2×) and brine, dried over Na$_2$SO$_4$, evaporated and purified by column chromatography (DCM/MeOH=1:0 to 25:1) to afford target compound 8 (539 mg). MS found: 467.4 [M+H]$^+$, 933.6 [2M+H]$^+$.

Example 9: (2-(2-(2',5'-Difluoro-[1,1'-biphenyl]-4-yl)-N-methylacetamido)-4-methylthiazol-5-yl)phosphonic acid

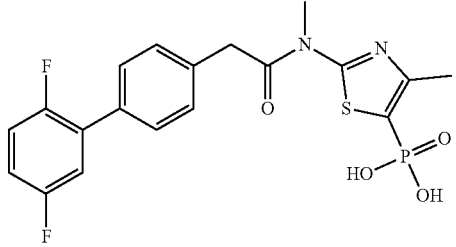

9

Ester 8 (539 mg) was dissolved in MeCN and cooled to −20° C., then TMSBr (1.5 mL) was added and the mixture was stirred at rt overnight. Additional TMSBr (1.5 mL) was added and the mixture was stirred at 45° C. for 2 h, poured into ice-cold EtOH, evaporated and consecutively coevaporated with EtOH, tert-BuOH and Et$_2$O. Lyophilisation from tert-BuOH afforded crude target compound 9 (620 mg). $^1$H-NMR (D$_2$O/THF-d$_8$/CD$_3$OD, 250 MHz) δ: 7.53-7.49 (m, 2H), 7.36 (d, 2H), 7.22-7.00 (m, 3H), 4.11 (s, 2H), 3.70 (s, 3H), 2.47 (d, 3H). MS found: 439.2 [M+H]$^+$, 877.4 [2M+H]$^+$.

Example 10 and Example 11: P-(2-(2-(2',5'-Difluoro-[1,1'-biphenyl]-4-yl)-N-methylacetamido)-4-methylthiazol-5-yl)phosphonamidic acid (10) and N-(5-(diaminophosphoryl)-4-methylthiazol-2-yl)-2-(2',5'-difluoro-[1,1'-biphenyl]-4-yl)-N-methylacetamide

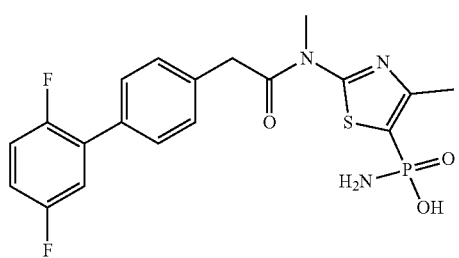

10

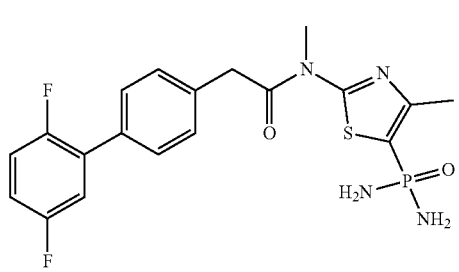

11

A solution of compound 9 (240 mg, 548 μmol) in dry THF (8 mL) was cooled to 0° C., then oxalyl chloride (71 μL, 822 μmol) and one drop DMF were added, stirred at 0° C. for 30 min and then 2 h at rt. Then additional oxalyl chloride (71 μL, 822 μmol) and two drops DMF were added, evaporated and two times coevaporated with THF. The remaining solid was dissolved in THF, cooled to −20° C. and quenched with 12% aq. NH$_3$. After 20 min EtOAc was added. The organic phase was neutralized with 6N HCl and extracted with EtOAc (2×). The combined organic layer was washed with water and brine, dried over Na$_2$SO$_4$, evaporated and purified by HPLC (H$_2$O/ACN+0.1% TFA=1:0 to 0:1) to afford a mixture of target compound 10 (17% by UV) and target compound 11 (82% by UV). Monoamide 10 MS found: 437.4 [M+H]$^+$, 873.5 [2M+H]$^+$; diamide 11 MS found: 438.4 [M+H]$^+$, 875.3 [2+H]$^+$.

Example 12: N-(5-(N-Cyanosulfamoyl)-4-methyl-thiazol-2-yl)-2-(2',5'-difluoro-[1,1-biphenyl]-4-yl)-N-methylacetamide

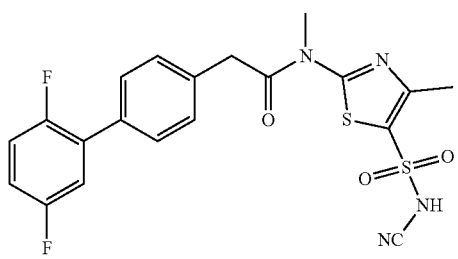

12

A solution of 2-(2',5'-difluoro-[1,1'-biphenyl]-4-yl)-N-methyl-N-(4-methyl-5-sulfamoylthiazol-2-yl)acetamide (200 mg, 458 μmol; prepared as described in WO2001/47904) in dry DMF (2 mL) was stirred with NaH (916 μmol, 37 mg of a 60% suspension in mineral oil) for 1 h at rt. TEA was added (4.6 mmol, 641 μL), and cooled to −20° C. Under cooling in an ice bath bromocyan (2.3 mmol, 242 mg) in dry DMF (2 mL) was added dropwise and the mixture was slowly warmed to rt and stirred for 16 h. The mixture was poured into water and extracted twice with EtOAc. The combined organic phase washed twice with 1M KHSO$_4$, sat. NaHCO$_3$, water, brine, dried with Na$_2$SO$_4$, filtered and evaporated. The product was dissolved in THF (2 mL) and precipitated with Et$_2$O (approx. 20 mL) to purified by HPLC to afford the target molecule 12 (38 mg, 18%). MS found: 463.2 [M+H]$^+$, 925.4 [2M+1-1]$^+$.

Example 13: N-[5-(N-Cyano-S-methyl-sulfinimi-doyl)-4-methyl-thiazol-2-yl]-2-[4-(2,5-difluorophe-nyl)phenyl]-N-methyl-acetamide

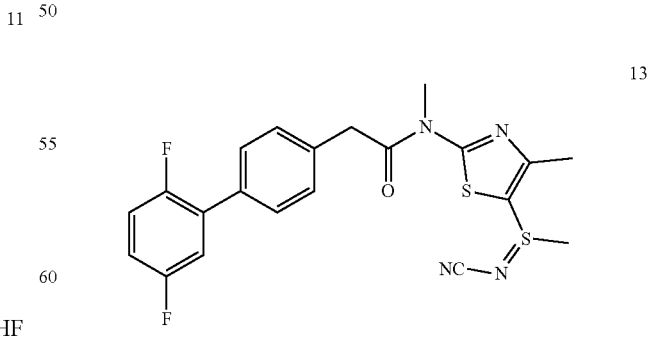

13

Intermediate P4b (250 mg, 619 μmol) and cyanamide (2 1.24 mmol, 52 mg) were dissolved in MeCN (3 mL) and cooled to −20° C. A cooled (−20° C.) solution of PhI(OAc)$_2$ (219 mg, 681 μmol) in MeCN (5 mL) was added. The solution was slowly warmed to rt and stirred for 2 h at rt. The product was precipitated with $Et_2O$ (approx. 30 mLI) and left at $-20°$ C. overnight. The precipitate was collected by centrifugation and washed with $Et_2O$. The precipitate contains the product at roughly 85% purity. The precipitate was suspended in MeCN (0.5 mL) and collected by centrifugation twice to obtain the target product 13 (98 mg, 35%). $^1$H-NMR ($CDCl_3+CD_3OD$, 300 MHz) δ: 7.56 (m, 2H), 7.40 (m, 2H), 7.16-7.04 (m, 3H), 4.17 (s, 2H), 3.82-3.81 (m, 3H), 3.21 (m, 3H), 2.59-2.58 (m, 3H). MS found: 445.3 $[M+H]^+$, 889.4 $[2M+H]^+$.

Example 14: N-[5-(N-Cyano-S-methyl-sulfonimidoyl)-4-methyl-thiazol-2-yl]-2-[4-(2,5-difluorophenyl)phenyl]-N-methyl-acetamide

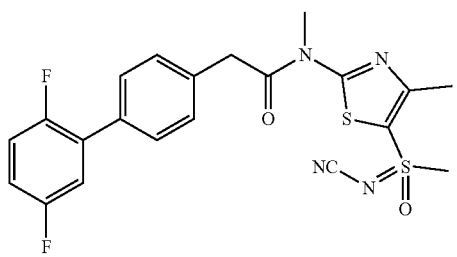

Example 13 (18 mg, 40 μmol) was dissolved in THF (1.5 mL). A solution of $NaIO_4$ (48 mg, 224 μmol) in $H_2O$ (800 μL) and $RuCl_3.H_2O$ (5.4 mg, 26 μmol) in $H_2O$ (300 μl) were added at rt and the mixture was vigorously stirred. After 5 min again 1 ml THF, 48 mg $NaIO_4$ dissolved in 800 μl $H_2O$ and 5.4 mg $RuCl_3 \times H_2O$ dissolved in 300 μl $H_2O$ were added. The reaction was stopped after 15 min (by pouring in water/EtOAc. The Product was extracted 2× with EE, the organic phase was washed with water (2×), sat. NaCl, dried over $Na_2SO_4$, filtered and concentrated to dryness. The product was purified by prep. RP-HPLC. Yield of compound 14 was 12 mg (26 μmol; 65%). $^1$H-NMR ($CDCl_3$, 300 MHz) δ: 7.57-7.54 (d, 2H), 7.37 (m, 2H), 7.14-7.01 (m, 3H), 4.11 (s, 2H), 3.77 (m, 3H), 3.40 (m, 3H), 2.66 (m, 3H). MS found 461.2 $[M+H]^+$, 921.4 $[2M+H]^+$.

Biological Assays

The compounds of the general Formula (I) and Formula (II) according to the invention exhibit an unforeseeable surprising spectrum of action. They exhibit not only an antiviral action especially against representatives of the Herpes viridae group, particularly against Herpes simplex viruses (HSV) but also improved solubility and a reduced carbonic anhydrase activity. These compound characteristics lead to an improved pharmacokinetic profile and consequently profound antiviral activity in vivo. They are thus suitable for the treatment and prophylaxis of disorders which are caused by viruses especially herpes viruses, in particular disorders which are caused by Herpes simplex viruses.

The compounds of the general Formula (I) and Formula (II) according to the invention exhibit an unforeseeable surprising reduced carbonic anhydrase activity.

The compounds thus show no or at least reduced off-target activity, in particular no or reduced side effects caused by carbonic anhydrase activity such as urothelial hyperplasia or diuretic pharmacological activity (G. Durand-Cavagna et al. *Fund. Appl. Toxicol.* 1992, 18:137).

The increased solubility improves formulation of the compounds, improves ADME characteristics and especially formulations used for intravenious applications.

The aqueous solubility (PBS, pH 7.4) was determined at Eurofins, Cerep, Panlabs according to C. A. Lipinski et al. *Adv. Drug Del. Rev.* 1997, 46:3.

In-Vitro Activity

Viruses and Cells:

HSV (HSV-1 Walki, HSV-1F, HSV-2 MS, HSV clinical isolates and HSV resistant strains) was cultivated on Vero cells (ATCC CCL-81) under the following conditions: The cells were grown in M199 medium (5% foetal calf serum, 2 mM glutamine, 100 IU/mL penicillin, 100 μg/mL streptomycin) in cell culture bottles at 37° C. and 5% $CO_2$. The cells were splitted twice per week (1:4). For the infection, the medium was removed, the cells were washed with Hank's solution, detached using 0.05% trypsin, 0.02% EDTA and incubacted at a density of $4 \times 10^5$ cells/mL under the above-mentioned conditions for 24 h. The medium was removed and the virus solution was added at an m.o.i of <0.05 in a volume of 2 mL per 175 cm$^2$ surface. The infected cells were incubated at 37° C., 5% $CO_2$ for 1 h and then the medium was made up to a volume of 50 mL per 175 cm$^2$ bottle. 3 days after the infection, the cultures showed clear signs of a cytopathic effect. The virus was released by freezing ($-80°$ C.) and thawing (37° C.) the infected cultures twice. Cell debris was removed by centrifugation (300 g, 10 min, 4° C.) and the supernatant was frozen in aliquots at $-80°$ C.

The virus titre was determined using a plaque assay. To this end, Vero cells were seeded in 24-well plates at a density of $4 \times 10^5$ cells per well and, after 24 h of incubation (37° C., 5% $CO_2$) infected with 100 μL of inoculum (dilutions ($10^{-2}$ to $10^{-12}$) of the virus stock). 1 h after the infection, the medium was removed and the cells were covered with 1 mL of overlay medium (0.5% methylcellulose, 0.22% sodium bicarbonate, 2 mM glutamine, 100 IU/mL penicillin, 100 μg/mL streptomycin, 5% foetal calf serum in MEM-Eagle medium with Earl's salt) and incubated for 3 d in a cell incubator at (37° C., 5% $CO_2$). The cells were then fixated using 4% formaline for 1 h, washed with water, stained with Giemsa for 30 min and then washed and dried. Using a plaque viewer, the virus titre was determined. The stocks used for the experiments had a titre of $1 \times 10^5$/mL up to $1 \times 10^8$/mL.

The antiviral action was determined using a patented (DE10235967 and WO2004/015416) and subsequently published activity selectivity assay (G. Kleymann et al. *J. Biomol. Screen.* 2004; 9:578) in 96- or 384-well mictrotitre plates using various cell lines of neuronal, lymphoid and epithelial origin, such as, for example, Vero (african green monkey kidney cells), MEF (murine embryonal fibroblasts), HELF (human embryonal fibroblasts), NT2 (human neuronal cell line) or Jurkat (human lymphoid T-cell line). The relevant experimental details of the above mentioned patent and publication to evaluate the antiviral activity of the invention (disclosed compounds) are described below.

The effect of the substances on the spreading of the cytopathogenic effect was determined in comparison to the reference compound acyclovir-sodium (Zovirax™), a clinically approved anti-herpes chemotherapeutic.

The compounds (50 mM stock solution dissolved in DMSO) are examined on microtitre plates (for example 96-well flat bottom cell culture plates) at a final concentration of 250 to 0.5 μM or, in case of potent antiviral compounds, 250 to 0.5 nM in 2 to 4 replications (4 to 2 substances per plate). Also examined are toxic and cytostatic effects or precipitation of the compounds. After an appropriate dilution of the compounds (1:2) on the microtitre plate in the appropriate medium (100 µL), a suspension of cells (50 µL, 1×10⁴ cells per well), such as, for example of Vero cells in M199 (medium 199 with 5% foetal calf serum, 2 mM glutamine and optionally 100 IU/ml penicillin and 100 µg/ml streptomycin) or of MEF or HELF cells in EMEM (Eagle's Minimum Essential Medium with 10% foetal calf serum, 2 mM glutamine and optionally 100 IU/mL penicillin and 100 µg/mL streptomycin), or of NT2- and Jurkat cells in DMEM ((4.5 mg/L glucose plus pyridoxin) with 10% foetal calf serum, 2 mM glutamine, 1 mM sodium pyruvate, non-essential amino acids and optionally 100 IU/mL penicillin and 100 µg/mL streptomycin) is added to each well and the cells in the relevant wells are infected with the appropriate amount of virus (HSV-1 or HSV-2 having an m.o.i (multiplicity of infection) of 0.0025 for Vero, HELF and MEF cells and an m.o.i. of 0.1 for NT2 and Jurkat cells). The plates are then incubated at 37° C. in a cell $CO_2$ incubator (5% $CO_2$) for several days. After this time, the cell lawn of, for example, Vero cells in the substance-free virus controls, starting from 25 infections centres, is completely destroyed or lysed by the cytopathogenic effect (CPE) of the Herpes viruses (100% CPE). The plates are initially evaluated visually using a microscope and then analysed using a fluorescent dye. To this end, the cell supernatant of all wells of the MTP is aspirated and the wells are filled with 250 µL PBS (phosphate buffered saline) wash solution. The PBS is then aspirated and all the wells are filled with 200 µL of fluorescent dye solution (fluroescein diacetate, 10 µg/mL in PBS). After an incubation time of 30 to 90 min, the test plates are read in a fluorescence detector at an excitation wavelength of 485 nm and an emission wavelength of 538 nm. Here, $IC_{50}$ is the half-maximal fluorescence intensity with respect to the non-infected cell control (100% value). The $IC_{50}$ value [%] ((compound treated infected cells minus non treated virus infected cells) divided by (cell control or Zovirax treated infected cells minus non treated infected cells)×100) can also be referenced to a suitable active compound control (see description of the assay: infected cells in the presence of suitable concentrations of an antiviral compound such as, for example, Zovirax 20 µM). This active compound control reaches fluorescence intensities of about 85 to 100% with respect to the non-infected cell control. The results for some compound are summarized in TA LE 1 below:

TABLE 1

| Example | $IC_{50}$ (HSV-1 infected Vero) | $IC_{50}$ (HSV-2 infected Vero) | $IC_{50}$ (HSV-1 ACV resistant) |
| --- | --- | --- | --- |
| 3 | 5-50 nM | 5-50 nM | 5-50 nM |
| 3-1 | 5-50 nM | 5-50 nM | 5-50 nM |
| 7 | 25-100 nM | 25-100 nM | 25-100 nM |
| 4 | 100-500 nM | 100-500 nM | 100-500 nM |
| 12 | 0.1-1 µM | 0.1-1 µM | 0.1-1 µM |
| 13 | 0.3-3 µM | 0.3-3 µM | 0.3-3 µM |
| 14 | 1-5 µM | 1-5 µM | 1-5 µM |
| P4b | 2-6 µM | 2-6 µM | 2-6 µM |
| 9 | 25-100 µM | 25-100 µM | 25-100 µM |
| Acyclovir | 0.5-3 µM | 0.5-3 µM | >25 µM |

Preference is given to antiviral compounds according to the invention whose $IC_{50}$ (HSV-1/Vero) in the activity selectivity assay described above is preferably below 100 µM, more preferably below 10 µM and very particularly preferable below 1 µM.

The compounds according to the invention are thus useful active compounds for the treatment and prophylaxis of disorders caused by viruses, in particular Herpes viruses and very particularly Herpes simplex viruses.

Surprisingly it turned out that also the intermediate compounds of the preparation methods as described herein exhibit good activity and suitability in the claimed indications. Accordingly, the invention further relates to the intermediate compounds as described herein (per se) and also to the respective medical use of those intermediates exhibiting the respective good activities and suitability.

Examples of indication areas which may be mentioned are:

1) Treatment and prophylaxis of herpes infections, in particular Herpes simplex infections in patients displaying Herpes labialis, Herpes genitalis and Herpes-related keratitis, Alzheimers disease, encephalitis, pneumonia, hepatitis etc.

2) Treatment and prophylaxis of herpes infections, in particular Herpes simplex infections, in patients with a suppressed immune system (for example AIDS patients, cancer patients, patients having a genetic immunodeficiency, transplant patients).

3) Treatment and prophylaxis of herpes infections, in particular Herpes simplex infections, in new-born children and infants 4) Treatment and prophylaxis of herpes infections, in particular Herpes simplex infections, and in Herpes-positive patients, in particular Herpes-simplex-positive patients, for suppressing recurrence (suppression therapy).

5) Treatment and prophylaxis of herpes infections, in particular Herpes simplex infections, and in Herpes-positive patients, in particular Herpes-simplex-positive patients, resistant to nucleosidic antiviral therapy such as acyclovir, penciclovir, famciclovir, ganciclovir, valacyclovir etc.

Carbonic Anhydrase Activity

Carbonic anhydrase II activity and its respective inhibition was performed according to R. Iyer et al. *J. Biomol. Screen.* 2006, 11:782 or in the case of carbonic anhydrase I activity according to A. R. Katritzky et al. *J. Med. Chem.* 1987, 30:2058 based on human starting material.

A protocol for determination of the carbonic anhydrase enymatic activity at rt using the pH indicator method is described below:

1 µL inhibitor (50 mM stock solution in DMSO) is diluted to a final test concentration ranging from 100 µM down to 1 nM (or 1 µL water in controls) and incubated for 2 min with 0.5 to 2 EU human Carboanhydrase I (180 U/mg) in 400 µL water and 200 µL phenol red indicator solution (20 mg/L). An enzymactic unit (EU) is defined as an amount which doubles the non catalyzed rate. The hydration reaction is initiated by adding 100 µL 0.5M bicarbonate buffer (0.3M $Na_2CO_3$; 0.2M $NaHCO_3$) and subsequent dumping of $CO_2$ through a needle (0.7×30 mm; 22G×1.25) into the assay solution at a rate of 10 mL gas/minute. The time to colour change (pH 7.2) is determined with a microchronometer or stop watch.

The percentage of inhibition is calculated as described below:

(time to color change without enzyme time to color change with enzyme and inhibitor)/(time to color change without enzyme time to color change with enzyme).

$IC_{50}$-values (inhibitory concentration) reflect the molar amount of inhibitor, which reduces the EU-activity in the test system by 50%.

In the test system no or reduced carbonic anhydrase inhibition is detected for Example 3 but in contrast to this finding Example 87 (WO2001/047904) shows carboanhydrase inhibition in the range of 1-3 μM ($IC_{50}$).

Results are shown below in TABLE 2:

TABLE 2

| Example | $IC_{50}$ (μM) Human Carboanhydrase II |
|---|---|
| 3 | >5 |
| reference example 87 (WO2001/47904) | 1.7 |
| acetazolamide | 0.026 |

Aqueous solubility (PBS, pH 7.4)

Measurement of the aqueous solubility was performed according to Lipinski, C. A. et al. (1997), *Adv. Drug Del. Rev.*, 46: 3-26. The relevant information from the literature is described below.

Aqueous solubility (μM, shake flask, 24 h incubation, RT) of a compound (10 mM Stock in DMSO) was determined by comparing the peak area (HPLC-UV/VIS) of the principal peak in a calibration standard (200 μM) containing organic solvent (methanol/water, 60/40, v/v) with the peak area of the corresponding peak in a buffer sample (PBS, pH 7.4). In addition, chromatographic purity (%) was defined as the peak area of the principal peak relative to the total integrated peak area in the HPLC chromatogram of the calibration standard.

In the aqueous solubility test system significantly increased solubility (at least one order of magnitude) is detected for Example 3 in comparison to Example 87 (WO2001/047904). Results are shown below in TABLE 3:

TABLE 3

| Example | Solubility [μM] (PBS, pH 7.4, 200 μM Test concentration) | Wavelength of Dectection [nm] | Chromatographic Purity [%] |
|---|---|---|---|
| 3 | 16.2 | 260 | 99 |
| reference example 87 (WO2001/47904) | 0.7 | 260 | 100 |
| Simvastatin | 18.7 | 230 | 100 |

In Vivo Activity

Pharmacokinetics

Pharmcokinetic parameters were determined for Example 3 in male mice strain C57BL/6J at an intraveneous (i.v.) dose of 5 mg/kg (5% DMSO in heterologous plasma, 2.5 ml/kg) and an oral dose (p.o) of 10 mg/kg (DMSO/0.5% HPMC (5:95), 5 ml/kg). The maximal plasma concentration at 10 mg/kg p.o reached 13.9 μM (cmax) 1 h (tmax) post administration. The terminal half life is ~3.5 h at an oral dose of 10 mg/kg and the respective bioavailability is 94%. Significant concentrations in the brain of treated mice (2-3 μM, 1000 ng compound/g brain) were detected 6 h post administration at an oral dose of 10 mg/kg.

Animal Model

Animal experiments were performed according to patent WO2001/047904 or subsequent publications (U. A. K. Betz et al. *Antimicrob. Agents Chemother.* 2002; 46:1766 or G. Kleymann et al. *Nat. Med.* 2002; 8:392). The relevant experimental details of the above mentioned patent and publication to evaluate the antiviral activity of the invention (disclosed compounds) in-vivo (animal models) are described below.

Animals:

6 week-old female mice, BALB/ABom strain were obtained from a commercial breeder.

Infection:

The animals were anaesthetized with $Et_2O$ in a sealed glass vessel. 50 μL of a dilution of the virus stock (infection dose $5\times10^4$ PFU (Plaque forming units)) were introduced into the nose of the anaesthetized animals using a pipette. In 90 to 100% of the animals, this infection dose causes death by generalized infection with prominent respiratory and central-nervous symptoms on average after 5 to 8 days.

Treatment and Assessment:

6 hours after infection animals were treated with doses of 0.1-150 mg/kg of body mass, 3 times per day at 7 am, 2 pm and 7 pm (tid) or 2 times per day at 7 am and 7 pm (bid) or once daily at 1 pm (od) for a period of 5 days. The compounds were pre-dissolved in DMSO and resuspended in 0.5% HPMC (hydroxypropylmethylcellulose) in water or PBS (DMSO/0.5% HPMC (max 5:95 ideally 1.5% DMSO, 0.5% HPMC in water or PBS)). After the last administration, the animals were monitored further and the time of death was determined.

A comparison of survival curves showed for the compound of Example 3, for example, an $ED_{50}$ of less than 10 mg/kg for HSV-1, were $ED_{50}$ means that 50% of the infected animals survive at this dose.

The novel active compounds can be converted in a known manner into customary formulations, such as tablets, caplets, sugar-coated tablets, pills, granules, aerosols, syrups, pharmaceutically suitable carriers and solvents. Here, the therapeutically active compound should in each case be present in a concentration of about 0.1 to 90% by weight of the total mixture, i.e. in amounts which are sufficient to achieve the dosage range indicated.

The formulations are prepared, for example, by extending the active compounds with solvents and/or excipients, if appropriate using emulsifiers and/or dispersants, if being possible, for example, if the diluent used is water, to use, if appropriate, organic solvents as auxiliary solvents.

Administration is carried out in a customary manner, preferably orally, parenterally or topically, in particular perlingually or intravenously.

In the case of parenteral administration, solutions of the active compounds using suitable liquid carrier materials can be employed.

In general, it has proved advantageous in the case or intravenous administration to administer amounts of from approx. 0.001 to 20 mg/kg, preferably approx. 0.01 to 10 mg/kg of bodyweight to achieve effective results, and in the case of oral administration the dose is approx. 0.01 to 30 mg/kg, preferably 0.1 to 20 mg/kg of body weight.

In spite of this, it may be necessary, if appropriate, to depart from the amounts mentioned, namely depending on the bodyweight or on the type of the administration route, on the individual response to the medicament, the manner of its formulation and the time or interval at which administration takes place. Thus, in some cases it may be adequate to manage with less than the abovementioned minimum amount, while in other cases the upper limit mentioned must be exceeded. In the case of administration of relatively large amounts it may be advisable to divide this into several individual administrations over the course of the day.

If appropriate, it may be useful to combine the compounds according to the invention with other active substances, in particular antiviral active compounds, so called combination therapy.

The invention claimed is:
1. A compound represented by Formula (I)

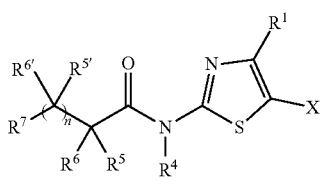

or an enantiomer, diastereomer, tautomer, N-oxide, formulation and pharmaceutically acceptable salt thereof, wherein:
X is selected from

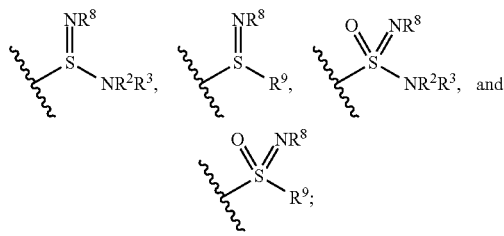

$R^1$ is selected from H, halogen, $C_{1-6}$-alkyl, halo-$C_{1-6}$-alkyl, $C_{3-6}$-cycloakyl, halo-$C_{3-6}$-cycloalkyl, —O—$C_{1-6}$-alkyl, —O-halo-$C_{1-6}$-alkyl and —NH—$C_{1-6}$-alkyl;
$R^2$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$cycloalkyl, $C_{0-10}$-alkylene-$C_{3-10}$-heterocycloalkyl, $C_{0-10}$-alkylene-(5- to 10-membered heteroaryl), $C_{0-10}$-alkylene-(6- to 10-membered aryl), $C_{0-10}$-alkylene-(6-to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C(=O)NR$^{11}$SO$_2$R$^{13}$, $C_{0-10}$-alkylene-C(=S)NR$^{11}$SO$_2$R$^{11}$, $C_{0-10}$-alkylene-C(=O)R$^{11}$, $C_{0-10}$-alkylene-C(=S)R$^{11}$, $C_{0-10}$-alkylene-SR$^{11}$, $C_{0-10}$-alkylene-SO$_x$R$^{13}$, $C_{0-10}$-alkylene-SO$_3$R$^{11}$, $C_{0-10}$-alkylene-SO$_2$NR$^{11}$R$^{12}$, $C_{0-10}$-alkylene-NR$^{11}$C(=O)R$^{11}$, $C_{0-10}$-alkylene-NR$^{11}$C(=S)R$^{11}$, $C_{0-10}$-alkylene-NR$^{11}$SO$_2$R$^{13}$, $C_{0-10}$-alkylene-NR$^{11}$C(=O)NR$^{11}$R$^{12}$, $C_{0-10}$-alkylene-NR$^{11}$C(=S))N$^{11}$R$^{12}$, $C_{0-10}$-alkylene-NR$^{11}$SO$_2$NR$^{11}$R$^{12}$, $C_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, —CN, —NO$_2$, OR$^{11}$, O—$C_{2-6}$-alkylene-OR$^{11}$, $C_{1-6}$-alkyl, halo-$C_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SR$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$, NR$^{11}$C(=O)NR$^{11}$R$^{12}$, NR$^{11}$SO$_2$NR$^{11}$R$^{12}$, $C_{3-10}$-cycloalkyl, O—$C_{3-10}$-cycloalkyl, $C_{3-10}$-heterocycloalkyl, O—$C_{3-10}$-heterocycloalkyl and NR$^{11}$R$^{12}$;
$R^3$ is selected from H, $C_{1-6}$-alkyl, halo-$C_{1-6}$-alkyl, —O—$C_{1-6}$-alkyl, —O-halo-$C_{1-6}$-alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;
or $R^2$ and $R^3$ when taken together with the nitrogen to which they are attached complete a 3- to 8-membered ring containing carbon atoms and optionally containing 1 or 2 additional heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;
$R^4$ is selected from H, $C_{1-6}$-alkyl, $C_{1-6}$-acyl, $C_{2-6}$-alkenyl, $C_{3-8}$-cycloalkyl and $C_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, $C_{1-3}$-alkyl, halo-$C_{1-3}$-alkyl, O—$C_{1-3}$-alkyl, O-halo-$C_{1-3}$-alkyl;
$R^5$ and $R^6$ and $R^{5'}$ and $R^{6'}$ are independently selected from H, halogen, $C_{1-6}$-alkyl, NH$_2$, NHC$_{1-6}$-alkyl, N(C$_{1-6}$-alkyl)$_2$, $C_{0-6}$-alkylene-C(=O)NH$_2$;
or $R^5$ and $R^6$ and $R^{5'}$ and $R^{6'}$ independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;
or $R^5$ and $R^{5'}$ and $R^6$ and $R^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, $C_{1-3}$-alkyl, halo-$C_{1-3}$-alkyl, O—$C_{1-3}$-alkyl, O-halo-$C_{1-3}$-alkyl, SO$_2$—$C_{1-3}$-alkyl, CO$_2$H;
$R^7$ is selected from a 6-membered aryl and 5- or 6-membered heteroaryl, wherein aryl and heteroaryl are optionally substituted with 1 to 4 substituents independently selected from halogen, —CN, —NO$_2$, OH, $C_{1-6}$-alkyl, O—$C_{1-6}$-alkyl, $C_{3-6}$-cycloalkyl, O—$C_{3-6}$-cycloalkyl, $C_{3-6}$-heterocycloalkyl, O—$C_{3-6}$-heterocycloalkyl, SO$_y$—$C_{1-6}$-alkyl, CO$_2$H, C(=O)O—$C_{1-6}$-alkyl, 6- to 10-membered aryl, 5- or 10-membered heteroaryl, O-(6- to 10-membered aryl) and O-(5- or 10-membered heteroaryl), wherein alkyl, cycloalkyl, heterocycloalkyl, aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)NR$^{11}$R$^{12}$, NR$^{11}$C(=O)NR$^{11}$R$^{12}$, NR$^{11}$C(=O)OR$^{13}$, OC(=O)NR$^{11}$R$^{12}$, C(=S)NR$^{11}$R$^{12}$, NR$^{11}$C(=S)NR$^{11}$R$^{12}$, NR$^{11}$C(=S)OR$^{13}$, OC(=S)NR$^{11}$R$^{12}$; SO$_y$—C$_{1-6}$-alkyl, SO$_y$-halo-$C_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$;
$R^8$ is selected from H, —CN, —NO$_2$, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5 to 10-membered heteroaryl), $C_{0-10}$-alkylene-(6 to 10-membered aryl), $C_{0-10}$-alkylene-(6 to 10-membered heteroaryl), $C_{0-10}$-alkylene-OR$^{11}$, $C_{0-10}$-alkylene-CO$_2$R$^{11}$, $C_{0-10}$-alkylene-C(=O)NR$^{11}$R$^{12}$, $C_{0-10}$-alkylene-C(=S)NR$^{11}$R$^{12}$, $C_{0-10}$-alkylene-C (=O)NR$^{11}$SO$_2$R$^{13}$, C$_{0-10}$-alkylene-C(=S)NR$^{11}$SO$_2$R$^{11}$, C$_{0-10}$-alkylene-C(=O)R$^{11}$, C$_{0-10}$-alkylene-C(=S)R$^{11}$, C$_{0-10}$-alkylene-SR$^{11}$, C$_{0-10}$-alkylene-SO$_x$—R$^{13}$, C$_{0-10}$-alkylene-SO$_3$R$^{11}$, C$_{0-10}$-alkylene-SO$_2$NR$^{11}$R$^{12}$, C$_{0-10}$-alkylene-NR$^{11}$C(=O)R$^{11}$, C$_{0-10}$-alkylene-NR$^{11}$C(=S)R$^{11}$, C$_{0-10}$-alkylene-NR$^{11}$SO$_2$R$^{11}$, C$_{0-10}$-alkylene-NR$^{11}$C(=O)NR$^{11}$R$^{12}$, C$_{0-10}$-alkylene-NR$^{11}$C(=S)NR$^{11}$R$^{12}$, C$_{0-10}$-alkylene-NR$^{11}$—SO$_2$—NR$^{11}$R$^{12}$, C$_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, —CN, —NO$_2$, OR$^{11}$, O—C$_{2-6}$-alkylene-OR$^{11}$, C$_{1-6}$-alkyl, halo-C$_{1-6}$-alkyl, halogen, CO$_2$R$^{11}$, CONR$^{11}$R$^{12}$, CONR$^{11}$SO$_2$R$^{11}$, COR$^{11}$, SO$_x$R$^{11}$, SO$_3$H, PO(OH)$_2$, SO$_2$NR$^{11}$R$^{12}$, NR$^{11}$COR$^{11}$, NR$^{11}$SO$_2$R$^{11}$, NR$^{11}$—CO—NR$^{11}$R$^{12}$, NR$^{11}$—SO$_2$—NR$^{11}$R$^{12}$, C$_{3-10}$-cycloalkyl, O—C$_{3-10}$-cycloalkyl, C$_{3-10}$-heterocycloalkyl, O—C$_{3-10}$-heterocycloalkyl and NR$^{11}$R$^{12}$;

R$^9$ is selected from C$_{1-10}$-alkyl, C$_{2-10}$-alkenyl, C$_{2-10}$-alkynyl, C$_{0-10}$-alkylene-C$_{3-10}$-cycloalkyl, C$_{0-10}$-alkylene-C$_{3-10}$-heterocycloalkyl, C$_{0-10}$-alkylene-(5- to 10-membered heteroaryl), C$_{0-10}$-alkylene-(6- to 10-membered aryl), C$_{0-10}$-alkylene-(6- to 10-membered heteroaryl), C$_{0-10}$-alkylene-OR$^{11}$, C$_{0-10}$-alkylene-CO$_2$R$^{11}$, C$_{0-10}$-alkylene-C(=O)NR$^{11}$R$^{12}$, C$_{0-10}$-alkylene-C(=S)NR$^{11}$R$^{12}$, C$_{0-10}$-alkylene-C(=O)NR$^{11}$SO$_2$R$^{13}$, C$_{0-10}$-alkylene-C(=S)NR$^{11}$SO$_2$R$^{11}$, C$_{0-10}$-alkylene-C(=O)R$^{11}$, C$_{0-10}$-alkylene-C(=S)R$^{11}$, C$_{0-10}$-alkylene-SR$^{11}$, C$_{0-10}$-alkylene-SO$_x$R$^{13}$, C$_{0-10}$-alkylene-SO$_3$R$^{11}$, C$_{0-10}$-alkylene-SO$_2$NR$^{11}$R$^{12}$, C$_{0-10}$-alkylene-NR$^{11}$C(=O)R$^{11}$, C$_{0-10}$-alkylene-NR$^{11}$C(=S)R$^{11}$, C$_{0-10}$-alkylene-NR$^{11}$SO$_2$R$^{13}$, C$_{0-10}$-alkylene-NR$^{11}$C(=O)NR$^{11}$R$^{12}$, C$_{0-10}$-alkylene-NR$^{11}$C(=S)NR$^{11}$R$^{12}$, C$_{0-10}$-alkylene-NR$^{11}$SO$_2$NR$^{11}$R$^{12}$, C$_{0-10}$-alkylene-NR$^{11}$R$^{12}$, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, —CN, —NO$_2$, OR$^{11}$, O—C$_{2-6}$-alkylene-OR$^{11}$, C$_{1-6}$-alkyl, halo-C$_{1-6}$-alkyl, halogen, CO$_2$R$^{11}$, C(=O)NR$^{11}$R$^{12}$, C(=O)NR$^{11}$SO$_2$R$^{11}$, C(=O)R$^{11}$, SO$_x$R$^{11}$, SO$_3$R$^{11}$, P(=O)(OR$^{11}$)$_2$, SO$_2$NR$^{11}$R$^{12}$, NR$^{11}$C(=O)R$^{11}$, NR$^{11}$SO$_2$R$^{13}$, NR$^{11}$C(=O)NR$^{11}$R$^{12}$, NR$^{11}$SO$_2$NR$^{11}$R$^{12}$, C$_{3-10}$-cycloalkyl, O—C$_{3-10}$-cycloalkyl, C$_{3-10}$-heterocycloalkyl, O—C$_{3-10}$-heterocycloalkyl and NR$^{11}$R$^{12}$;

R$^{11}$ is independently selected from H, C$_{1-6}$-alkyl, C$_{0-6}$-alkylene-C$_{3-10}$-cycloalkyl and C$_{0-6}$-alkylene-C$_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, C$_{1-3}$-alkyl, halo-C$_{1-3}$-alkyl, O—C$_{1-3}$-alkyl, O-halo-C$_{1-3}$-alkyl, NH$_2$, NH(C$_{1-3}$-alkyl), N(C$_{1-3}$-alkyl)$_2$, C$_{3-6}$-heterocycloalkyl, C$_{3-6}$-cycloalkyl, SO$_2$—NHC$_{1-3}$-alkyl, SO$_2$—N(C$_{1-3}$-alkyl)$_2$ and SO$_2$—C$_{1-3}$-alkyl, wherein cycloalkyl and heterocycloalkyl is unsubstituted or substituted with 1 to 3 substituents independently selected from the group consisting of F, OH, oxo, CH$_3$, CHF$_2$ and CF$_3$;

R$^{12}$ is independently selected from H, C$_{1-6}$-alkyl, halo-C$_{1-6}$-alkyl and C$_{3-6}$-cycloalkyl;

or R$^{11}$ and R$^{12}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, —CN, —NO$_2$, OH, oxo, C$_{1-3}$-alkyl, halo-C$_{1-3}$-alkyl, O—C$_{1-3}$-alkyl, O-halo-C$_{1-3}$-alkyl, SO$_2$—C$_{1-3}$-alkyl, CO$_2$H;

R$^{13}$ is independently selected from C$_{1-6}$-alkyl, C$_{0-6}$-alkylene-C$_{3-10}$-cycloalkyl and C$_{0-6}$-alkylene-C$_{3-10}$-heterocycloalkyl, wherein alkyl, alkylene, cycloalkyl and heterocycloalkyl is unsubstituted or substituted with 1 to 6 substituents independently selected from the group consisting of halogen, —CN, OH, oxo, C$_{1-3}$-alkyl, halo-C$_{1-3}$-alkyl, O—C$_{1-3}$-alkyl, O-halo-C$_{1-3}$-alkyl, NH$_2$, NH(C$_{1-3}$-alkyl), N(C$_{1-3}$-alkyl)$_2$, C$_{3-6}$-heterocycloalkyl, C$_{3-6}$-cycloalkyl, SO$_2$—NHC$_{1-3}$-alkyl, SO$_2$—N(C$_{1-3}$-alkyl)$_2$ and SO$_2$—C$_{1-3}$-alkyl, wherein cycloalkyl and heterocycloalkyl is unsubstituted or substituted with 1 to 3 substituents independently selected from the group consisting of F, OH, oxo, CH$_3$, CHF$_2$ and CF$_3$;

n is selected from 0 and 1;

x is independently selected from 1 and 2;

y is independently selected from 0, 1 and 2;

and wherein optionally R$^1$ is connected to one residue selected from R$^2$, R$^3$, R$^8$, R$^9$, or R$^{12}$ to form a 5 to 8-membered heterocycle, which is optionally substituted with 1 to 4 substituents independently selected from the group consisting of halogen, —ON, —NO$_2$, OH, oxo, C$_{1-3}$-alkyl, halo-C$_{1-3}$-alkyl, O—C$_{1-3}$-alkyl, O-halo-C$_{1-3}$-alkyl, SO$_2$—C$_{1-3}$-alkyl, CO$_2$H.

2. The compound according to claim 1, wherein:

R$^4$ is selected from C$_{1-6}$-alkyl, C$_{1-6}$-acyl, C$_{3-8}$-cycloalkyl and C$_{3-8}$-heterocycloalkyl, wherein alkyl, acyl, alkenyl, cycloalkyl and heterocycloalkyl are optionally substituted with 1 to 5 substituents independently selected from halogen, —CN, OH, oxo, C$_{1-3}$-alkyl, halo-C$_{1-3}$-alkyl, O—C$_{1-3}$-alkyl, O-halo-C$_{1-3}$-alkyl;

R$^5$ and R$^6$ and R$^{5'}$ and R$^{6'}$ are independently selected from H and C$_{1-3}$-alkyl;

or R$^5$ and R$^6$ and R$^{5'}$ and R6' independently when taken together with the carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, OH, oxo, Me (—CH$_3$), OMe (—O—CH$_3$), CHF$_2$, CF$_3$, OCHF$_2$, OCF$_3$;

or R$^5$ and R$^{5'}$ and R$^6$ and R$^{6'}$ independently when taken together with the two adjacent carbon to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, OH, oxo, Me (—CH$_3$), OMe (—O—CH$_3$), CHF$_2$, CF$_3$, OCHF$_2$, OCF$_3$;

R$^7$ is selected from a 6-membered aryl and 5- or 6-membered heteroaryl, wherein aryl and heteroaryl are optionally substituted with 1 to 3 substituents independently selected from halogen, OH, Me (—CH$_3$), OMe (—O—CH$_3$), CHF$_2$, CF$_3$, OCHF$_2$, OCF$_3$ and substituted with 6-membered aryl and 5- or 6-membered heteroaryl, wherein aryl and heteroaryl are optionally substituted with 1 to 5 substituents independently selected from halogen, —CN, —NO$_2$, OH, R$^{13}$, OR$^{13}$, CO$_2$R$^{11}$, NR$^{11}$R$^{12}$, C(=O)R$^{11}$, C(=S)R$^{11}$, C(=O)

NR$^{11}$R$^{12}$, NR$^{11}$C(=O)NR$^{11}$R$^{12}$, NR$^{11}$C(=O)OR$^{13}$, OC(=O)NR$^{11}$R$^{12}$, C(=S)NR$^{11}$R$^{12}$, NR$^{11}$C(=S)NR$^{11}$R$^{12}$, NR$^{11}$C(=S)OR$^{13}$, OC(=S)NR$^{11}$R$^{12}$; SO$_y$—C$_{1-6}$-alkyl, SO$_y$-halo-C$_{1-6}$-alkyl, SR$^{11}$, SO$_x$R$^{13}$, SO$_3$R$^{11}$, SO$_2$NR$^{11}$R$^{12}$, NR$^{11}$SO$_2$R$^{13}$, NR$^{11}$SO$_2$NR$^{11}$R$^{12}$; and the remaining substituents have the meaning as defined in claim 1.

3. The compound according to claim 1, wherein R$^7$ is phenyl, optionally substituted with 1 to 4 substituents (R$^x$), wherein the 1 to 4 substituents R$^x$ independently have the meaning of the possible substituents of R$^7$ as defined in claim 1 and which is represented by Formula (II)

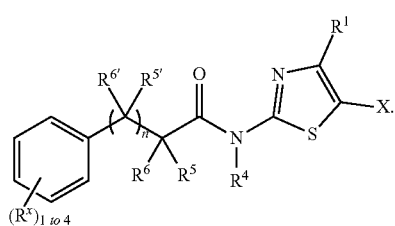

4. The compound according to claim 1, wherein R$^7$ is selected from

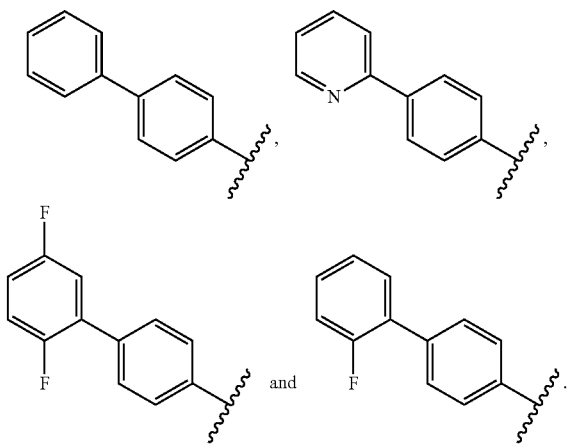 [SMILES: *c1ccc(-c2ccccc2)cc1 ; *c1ccc(-c2ccccn2)cc1 ; *c1ccc(-c2cc(F)ccc2F)cc1 ; *c1ccc(-c2ccccc2F)cc1]

5. The compound according to claim 1, wherein:
X is selected from

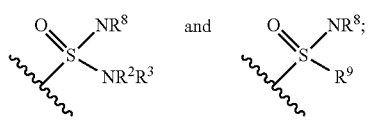

and
R$^1$ is selected from H, halogen, C$_{1-6}$-alkyl, halo-C$_{1-6}$-alkyl, C$_{3-6}$-cycloalkyl, halo-C$_{3-6}$-cycloalkyl, —O—C$_{1-6}$-alkyl, —O-halo-C$_{1-6}$-alkyl and —NH—C$_{1-6}$-alkyl.

6. The compound according to claim 1, wherein:
R$^2$ and R$^3$ are independently selected from H, C$_{1-3}$-alkyl, halo-C$_{1-3}$-alkyl, —O—C$_{1-3}$-alkyl, —O-fluoro-C$_{1-3}$-alkyl, C$_{3-6}$-cycloalkyl and C$_{3-6}$-heterocycloalkyl, wherein alkyl, cycloalkyl and heterocycloalkyl are optionally substituted with 1 to 5 substituents independently selected from F, Cl, OH, oxo, Me (—CH$_3$), CHF$_2$ and CF$_3$;

or R$^2$ and R$^3$ when taken together with the nitrogen to which they are attached complete a 5- to 6-membered ring containing carbon atoms and optionally containing one additional heteroatom selected from O, S or N, wherein the ring is unsubstituted or substituted with 1 to 4 substituents independently selected from the group consisting of F, Cl, OH, oxo, Me (—CH$_3$), CHF$_2$ and CF$_3$;

R$^8$ is selected from H, —CN, —NO$_2$, OH, C$_{1-3}$-alkyl, O—C$_{1-3}$-alkyl, fluoro-C$_{1-3}$-alkyl and O-fluoro-C$_{1-3}$-alkyl, R$^9$ is selected from C$_{1-3}$-alkyl, t-butyl, fluoro-C$_{1-3}$-alkyl, and -cyclopropyl; and R$^{12}$ is independently selected from H, Me (—CH$_3$) and Et (—CH$_2$—CH$_3$).

7. The compound according to claim 1, wherein n is 0.

8. The compound according to claim 1, wherein the compound is selected from:

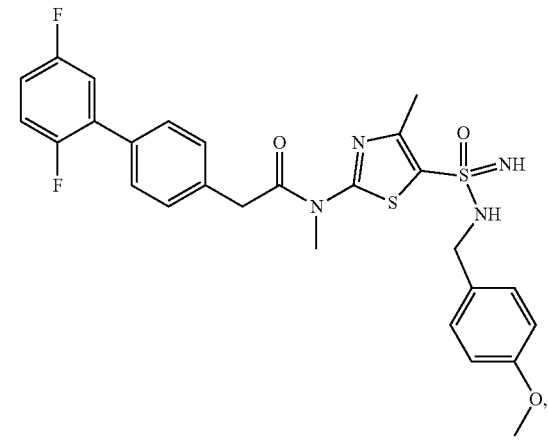

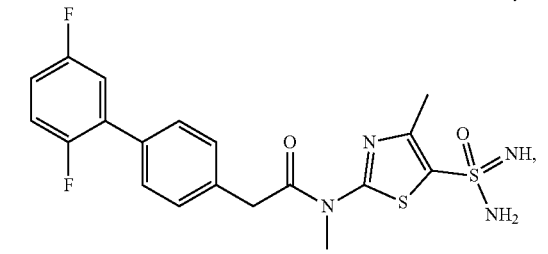

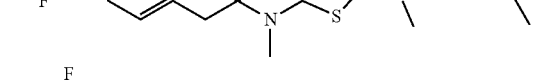
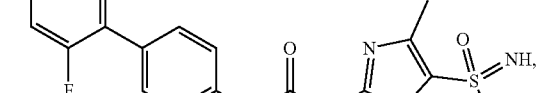

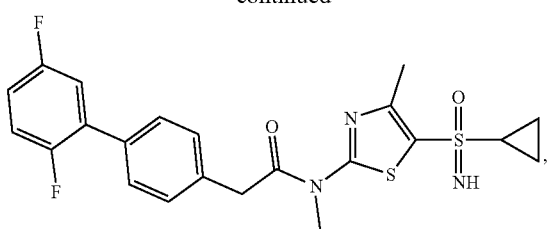
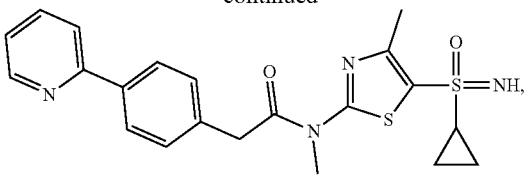
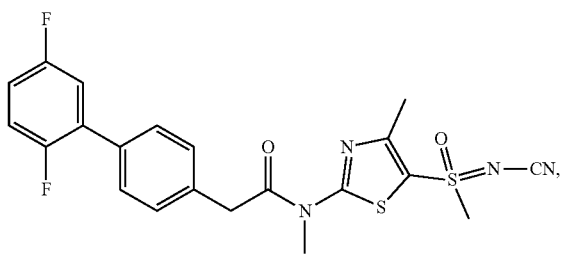
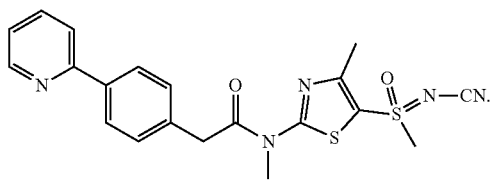

9. A medicament for the treatment or prophylaxis of a disease or disorder associated with viral infections of a patient, the medicament comprising the compound according to claim 1 and one or more selected from a pharmaceutically acceptable carrier and excipients.

10. A method of treatment or prophylaxis of a disease or disorder associated with viral infections, the method comprising a step of administering to a patient in need thereof, an effective amount of the compound according to claim 1.

11. The method according to claim 10, wherein the disease or disorder is associated with viral infections caused by herpes viruses.

12. A method of treatment or prophylaxis of neurodegenerative diseases caused by viruses, the method comprising a step of administering to a patient in need thereof, an effective amount of the compound according to claim 1.

13. The method according to claim 10, wherein:

the disease or disorder associated with viral infections includes herpes infections, Alzheimers disease, encephalitis, pneumonia, hepatitis, and a suppressed immune system, the effective amount of the compound according to claim 1 is administered to AIDS patients, cancer patients, patients having a genetic immunodeficiency, transplant patients, new-born children, infants, Herpes-positive patients, and the effective amount of the compound suppresses recurrence of the disease or disorder in patients who are resistant to nucleosidic antiviral therapy.

14. A pharmaceutical composition comprising one or more of the compounds according to claim 1 and at least one pharmaceutically acceptable carrier and/or excipient and/or at least one further active substance being effective in treating a disease or disorder associated with viral infections.

15. The compound according to claim 4, wherein R⁷ is

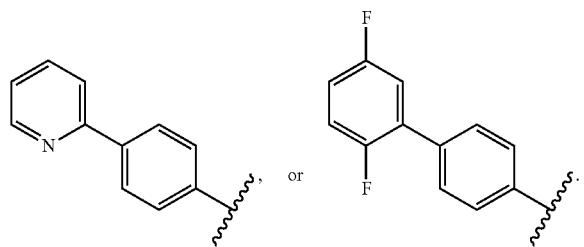 [SMILES: *c1ccc(-c2ccccn2)cc1 ; *c1ccc(-c2cc(F)ccc2F)cc1]

16. The compound according to claim 2, wherein R⁷ is phenyl, optionally substituted with 1 to 4 substituents (Rˣ), wherein the 1 to 4 substituents Rˣ independently have the meaning of the possible substituents of R⁷ as defined in claim 2 and which is represented by Formula (II)

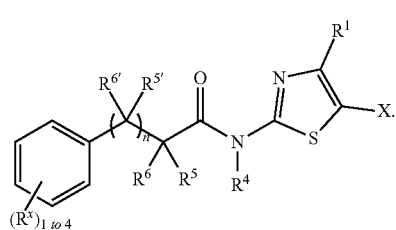

17. The compound according to claim 2, wherein R⁷ is selected from

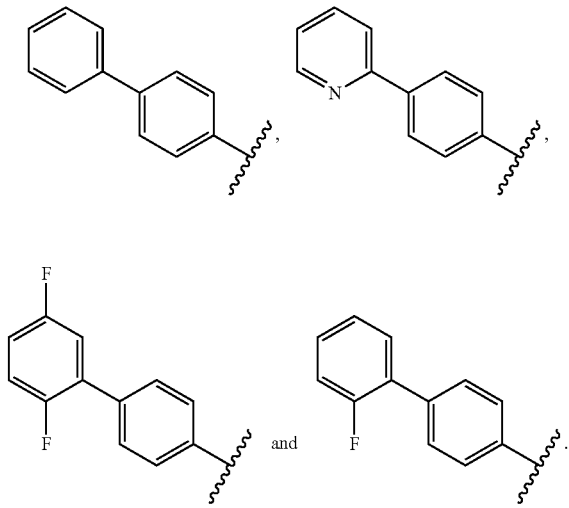

18. The compound according to claim 2, wherein:

X is selected from

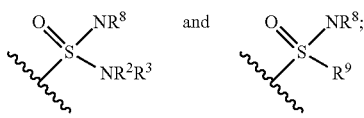

and

R¹ is selected from H, halogen, $C_{1-6}$-alkyl, halo-$C_{1-6}$-alkyl, $C_{3-6}$-cycloalkyl, halo-$C_{3-6}$-cycloalkyl, —O—$C_{1-6}$-alkyl, —O-halo-$C_{1-6}$-alkyl and —NH—$C_{1-6}$-alkyl.

19. The compound according to claim 2, wherein:

R² and R³ are independently selected from H, $C_{1-3}$-alkyl, halo-$C_{1-3}$-alkyl, —O—$C_{1-3}$-alkyl, —O-fluoro-$C_{1-3}$-alkyl, $C_{3-6}$-cycloalkyl and $C_{3-6}$-heterocycloalkyl, wherein alkyl, cycloalkyl and heterocycloalkyl are optionally substituted with 1 to 5 substituents independently selected from F, Cl, OH, oxo, Me (—CH₃), CHF₂ and CF₃;

or R² and R³ when taken together with the nitrogen to which they are attached complete a 5- to 6-membered ring containing carbon atoms and optionally containing one additional heteroatom selected from O, S or N, wherein the ring is unsubstituted or substituted with 1 to 4 substituents independently selected from the group consisting of F, Cl, OH, oxo, Me (—CH₃), CHF₂ and CF₃;

R⁸ is selected from H, —CN, —NO₂, OH, $C_{1-3}$-alkyl, O—$C_{1-3}$-alkyl, fluoro-$C_{1-3}$-alkyl and O-fluoro-$C_{1-3}$-alkyl;

R⁹ is selected from $C_{1-3}$-alkyl, t-butyl, fluoro-$C_{1-3}$-alkyl, and -cyclopropyl;

R¹⁰ is selected from —CN, OH, and —NO₂; and

R¹² is independently selected from H, Me (—CH₃) and Et (—CH₂—CH₃).

20. The method according to claim 13, wherein:

the disease or disorder associated with viral infections includes Herpes labialis, Herpes genitalis, or Herpes-related keratitis;

the effective amount of the compound according to claim 1 is administered to Herpes-simplex-positive patients; and the effective amount of the compound suppresses recurrence of the disease or disorder in patients who are resistant to acyclovir antiviral therapy, penciclovir antiviral therapy, famciclovir antiviral therapy, ganciclovir antiviral therapy, or valacyclovir antiviral therapy.

* * * * *